(12) United States Patent
Ellison et al.

(10) Patent No.: US 12,419,524 B2
(45) Date of Patent: *Sep. 23, 2025

(54) SYSTEMS AND METHODS FOR TOUCHLESS TEMPERATURE SCREENING SYSTEM

(71) Applicant: Walmart Apollo, LLC, Bentonville, AR (US)

(72) Inventors: Benjamin R. Ellison, San Francisco, CA (US); Eric Chad Neipling, Rogers, AR (US); Addison K. Bostian, Centerton, AR (US); Manideep Pabba, Bentonville, AR (US); Ryan J. Giovacchini, Rogers, AR (US); Alisha D. Fleshman, Centerton, AR (US); Kipp S. Coco, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/233,539

(22) Filed: Aug. 14, 2023

(65) Prior Publication Data

US 2023/0380696 A1 Nov. 30, 2023

Related U.S. Application Data

(63) Continuation of application No. 17/505,405, filed on Oct. 19, 2021, now Pat. No. 11,766,181.

(Continued)

(51) Int. Cl.
*A61B 5/01* (2006.01)
*A61B 5/00* (2006.01)
(Continued)

(52) U.S. Cl.
CPC .............. *A61B 5/015* (2013.01); *A61B 5/117* (2013.01); *A61B 5/742* (2013.01); *A61B 5/7495* (2013.01);
(Continued)

(58) Field of Classification Search
CPC ......... A61B 5/015; A61B 5/117; A61B 5/742; A61B 5/7495; A61B 2562/18; A61B 5/11;
(Continued)

(56) References Cited

U.S. PATENT DOCUMENTS 8,629,755 B2 1/2014 Hashim-Waris
8,730,007 B2 5/2014 Otake
(Continued)

FOREIGN PATENT DOCUMENTS

KR 101912390 B1 10/2018
KR 102134903 B1 7/2020
WO WO-2011005224 A1 * 1/2011 ............... A61B 5/01

OTHER PUBLICATIONS

Sharma, C., Design U.S. Appl. No. 29/755,299, filed Oct. 19, 2020.
(Continued)

*Primary Examiner* — John E Breene
*Assistant Examiner* — Janice M Soto
(74) *Attorney, Agent, or Firm* — Foley IP Law, PLLC

(57) ABSTRACT

In some embodiments, apparatuses and methods are provided herein useful to screening a body temperature of a human. In some embodiments, there is provided a temperature screening system that screens a body temperature of a human including a housing comprising an output interface; one or more first sensors; a temperature sensor; and a control circuit configured to: cause the output interface to provide one or more messages; receive the one or more user inputs indicative of responses to at least one of the one or more (Continued)

messages; receive temperature data corresponding to the body temperature; determine whether the human meets a health criteria; and transmit a control signal indicative of the human meeting the health criteria in response to the human meeting the health criteria.

19 Claims, 32 Drawing Sheets

Related U.S. Application Data

(60) Provisional application No. 63/209,595, filed on Jun. 11, 2021, provisional application No. 63/093,737, filed on Oct. 19, 2020.

(51) Int. Cl.
| | | |
|---|---|---|
| A61B 5/117 | (2016.01) | |
| G01J 5/00 | (2022.01) | |
| G01J 5/02 | (2022.01) | |
| G01J 5/04 | (2006.01) | |
| G16H 40/63 | (2018.01) | |

(52) U.S. Cl.
CPC .............. *G01J 5/0025* (2013.01); *G01J 5/026* (2013.01); *G01J 5/04* (2013.01); *G16H 40/63* (2018.01); *A61B 2562/18* (2013.01)

(58) Field of Classification Search
CPC .... A61B 2562/08; G01J 5/0025; G01J 5/026; G01J 5/04; G01J 5/025; G16H 40/63; G16H 50/20
See application file for complete search history.

(56) References Cited

U.S. PATENT DOCUMENTS

| | | | |
|---|---|---|---|
| 9,307,912 B2 | 4/2016 | Mullin et al. | |
| 9,398,856 B2 | 7/2016 | Abreu | |
| 9,712,749 B2 * | 7/2017 | Lombardi | G06F 3/147 |
| 11,656,687 B2 | 5/2023 | Kim | |
| D989,278 S | 6/2023 | Giovacchini | |
| 11,766,181 B2 | 9/2023 | Ellison | |
| 11,776,082 B2 | 10/2023 | Gatta | |
| 11,850,749 B2 | 12/2023 | Yang | |
| 2007/0150916 A1 * | 6/2007 | Begole | H04N 21/42201 |
| | | | 382/116 |
| 2008/0018480 A1 | 1/2008 | Sham | |
| 2008/0212746 A1 | 9/2008 | Gupta et al. | |
| 2009/0217076 A1 | 8/2009 | Okuhara | |
| 2009/0222671 A1 | 9/2009 | Burbank et al. | |
| 2012/0075463 A1 | 3/2012 | Chen et al. | |
| 2013/0050425 A1 * | 2/2013 | Im | G06F 3/0304 |
| | | | 348/46 |
| 2013/0226354 A9 | 8/2013 | Ruff et al. | |
| 2013/0271590 A1 | 10/2013 | Saint Clair et al. | |
| 2015/0182127 A1 | 7/2015 | Heller | |
| 2016/0113517 A1 | 4/2016 | Lee et al. | |
| 2020/0371599 A1 | 11/2020 | Lee | |
| 2020/0372743 A1 | 11/2020 | Miller | |
| 2020/0410790 A1 | 12/2020 | Thompson | |
| 2021/0304537 A1 | 9/2021 | Reed et al. | |
| 2021/0369122 A1 | 12/2021 | Lane | |
| 2022/0036678 A1 | 2/2022 | Parekh | |
| 2022/0117496 A1 | 4/2022 | Ellison et al. | |

OTHER PUBLICATIONS

PCT; App. No. PCT/US2021/055510; International Search Report and Written Opinion mailed Jan. 26, 2022; Docket No. 8842-150608-WO; 27 pages.

Non-Final Office Action issued May 29, 2024 in connection with U.S. Appl. No. 17/505,388, 42 pages.

Final Office Action issued Oct. 10, 2024 in connection with U.S. Appl. No. 17/505,388, 27 pages.

Non-Final Office Action issued Feb. 6, 2025 in connection with U.S. Appl. No. 17/505,388, 24 pages.

* cited by examiner

Health Screening

Have you had any of the following symptoms in the past 10 days - not due to any other cause diagnosed by a healthcare provider?

Fever or chills, fatigue, nausea or vomiting, diarrhea, muscle or body aches, headache, sore throat, dry cough or difficulty breath, new loss of taste or smell, congestion or runny nose Exit in 20s Yes    No

SYSTEMS AND METHODS FOR TOUCHLESS TEMPERATURE SCREENING SYSTEM

CROSS-REFERENCE TO RELATED APPLICATION(S)

This application is a continuation of U.S. application Ser. No. 17/505,405 filed Oct. 19, 2021, which claims the benefit of U.S. Provisional Application No. 63/093,737 filed Oct. 19, 2020, and U.S. Provisional Application No. 63/209,595 filed Jun. 11, 2021, all of which are incorporated herein by reference in their entirety.

TECHNICAL FIELD

This invention relates generally to screening a body temperature of a human.

BACKGROUND

During periods of time involving the spread of infectious disease and illness, everyone is more aware of his/her surrounding and the health effect of the people he/she frequently and temporarily interacts with. Generally, it may be desired to screen for the health of the person seeking entry to a facility, for example, by taking the temperature of the person seeking entry. In the case of a business, prior to entering a facility of the business, an employee of a business may be individually asked a number of health questions by a designated employee, then followed by the designated employee taking a body temperature of the employee.

BRIEF DESCRIPTION OF THE DRAWINGS

Disclosed herein are embodiments of systems, apparatuses and methods pertaining to screening a health status, e.g., including body temperature, of a human using a touchless health screening system. This description includes drawings, wherein:

FIGS. 8-30 are illustrative graphical user interfaces showing exemplary steps in an exemplary process of touchless screening of a body temperature of a human in accordance with some embodiments;

Figure 1:
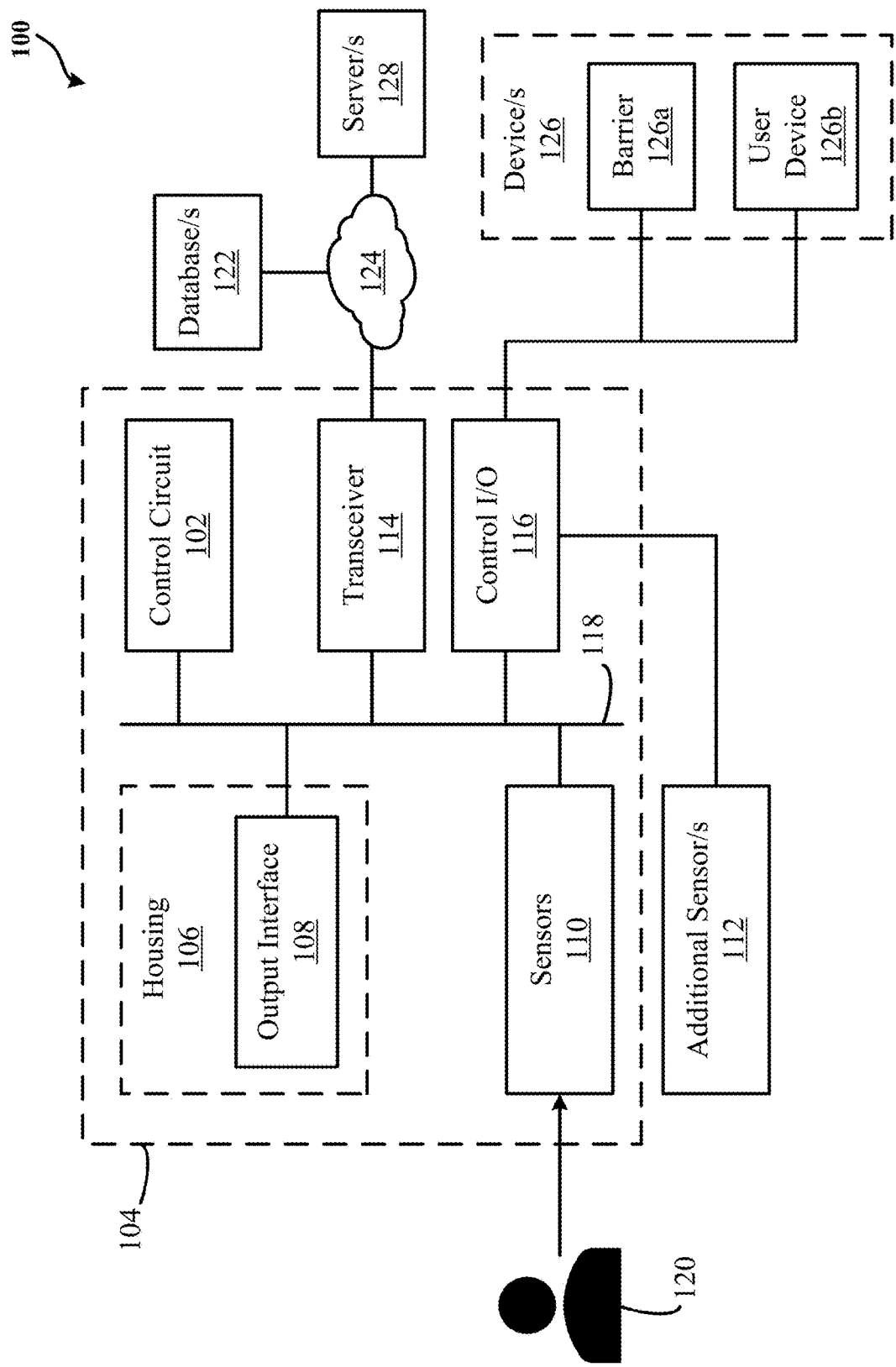
FIG. 1 illustrates a simplified block diagram of an exemplary system for touchless screening of a body temperature of a human in accordance with some embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein useful for touchless screening of a health status, e.g., a body temperature, of a human. In some embodiments, touchless temperature screening systems and corresponding methods are provided that screen a body temperature of a human. In some embodiments, the system includes a housing that may include an output interface that provides one or more messages to the human being screened. In some embodiments, the human is one of an employee of a retail entity, an employee of a vendor of the retail entity, and/or a visitor seeking access to a facility of the retail entity. In some embodiments, the human is one of a person seeking access to an area, a person seeking approval to perform a task, and/or a person seeking passage. In some embodiments, the system and method includes a plurality of sensors. In some embodiments, at least one of the plurality of sensors captures an identification information associated with the human. In some embodiments, at least one of the plurality of sensors receives one or more user inputs from the human. In some embodiments, at least one of the plurality of sensors detects a body temperature of the human, e.g., it senses data that corresponds to the body temperature of the human. In some embodiments, systems and methods described herein limit human contact with the screening systems which can help to limit exposure to and the spread of infectious illnesses and diseases among users of the screening systems. Further, in some embodiments, the systems and methods provided do not require a human administrator of the screening process to be present while humans are being screened.

In some embodiments, the systems and methods include a control circuit coupled to the output interface and/or the plurality of sensors. The control circuit may receive, via at least one of the plurality of sensors, the identification information associated with the human. In some embodiments, the control circuit causes the output interface to provide the one or more messages to the human being screened. In some embodiments, the control circuit receives, via at least one of the plurality of sensors, the one or more user inputs from the human indicative of responses to at least one of the one or more messages. In some embodiments, the control circuit receives, via the at least one of the plurality of sensors, data corresponding to the body temperature of the human. For example, in some embodiments, the data includes an estimated temperature of the human, includes measurements or values that correspond to the temperature of the human or includes measurements or values useful to calculate the temperature of the human. In some embodiments, the control circuit determines, based on the received one or more user inputs and/or the received temperature data, whether the human meets a health criteria, e.g., whether the human's body temperature is in an acceptable range for the intended purpose of the health screen. In some embodiments, the control circuit causes the output interface to provide a message indicating whether the human has met the health criteria.

In some embodiments, a touchless temperature screening system that screens a body temperature of a human without a direct or an indirect physical contact from the human includes a housing including an output interface that provides one or more messages to a human. In some embodiments, the system includes one or more first sensors of a plurality of sensors coupled to the housing. In some embodiments, the one or more first sensors receive one or more user inputs from the human without physical contact from the human or an extension of the human. In some embodiments, the system includes a temperature sensor of the plurality of sensors coupled to the housing. In some embodiments, the temperature sensor detects a body temperature of the human without physical contact from the human or the extension of the human. In some embodiments, the system includes a control circuit coupled to the output interface and the plurality of sensors. In some embodiments, the control circuit causes the output interface to provide the one or more messages to the human. In some embodiments, the control circuit receives, via the one or more first sensors, the one or more user inputs from the human indicative of responses to at least one of the one or more messages. In some embodiments, the control circuit receives, via the temperature sensor, temperature data corresponding to the body temperature of the human. In some embodiments, the control circuit determines, based on the received one or more user inputs and the received temperature data, whether the human meets a health criteria. In some embodiments, the control circuit, in response to the human meeting the health criteria, transmit a control signal indicative of the human meeting the health criteria.

In some embodiments, a method for touchless temperature screening system that screens a body temperature of a human without a direct or an indirect physical contact from the human includes causing, by a control circuit, an output interface coupled to a housing to provide one or more messages to a human. In some embodiments, the method includes receiving, by one or more first sensors of a plurality of sensors coupled to the housing, one or more user inputs from the human without physical contact from the human or an extension of the human, wherein the one or more user inputs are indicative of responses by the human to at least one of the one or more messages. In some embodiments, the method includes receiving, by the control circuit via a temperature sensor of the plurality of sensors coupled to the housing and without physical contact from the human or the extension of the human, temperature data corresponding to a body temperature of the human. In some embodiments, the method includes determining, by the control circuit based on the received one or more user inputs and the received temperature data, whether the human meets a health criteria. In some embodiments, the method includes, in response to the human meeting the health criteria, transmitting, by the control circuit, a control signal indicative of the human meeting the health criteria.

To illustrate various embodiments, FIGS. 1-32 are described below that variously illustrate touchless or contactless health screening systems and methods. In some embodiments, the touchless temperature screening system is completely touchless or contactless meaning humans that are using the system interact with and/or use the system without a direct or an indirect physical contact from the humans. A direct physical contact is understood to include, for example, a portion of the human physically touching or contacting a portion of the system. An indirect physical contact is understood to include, for example, an instrument or tool held by manipulated by a human or a garment, shield or glove worn by or contacting the human, where the instrument, tool, garment, shield, glove (rather than the portion of the human) physically touches or contacts a portion of the system. In some embodiments, a touchless temperature screening system does not provide any direct or indirect physical contact from a hand and/or finger of the human.

Figure 6:
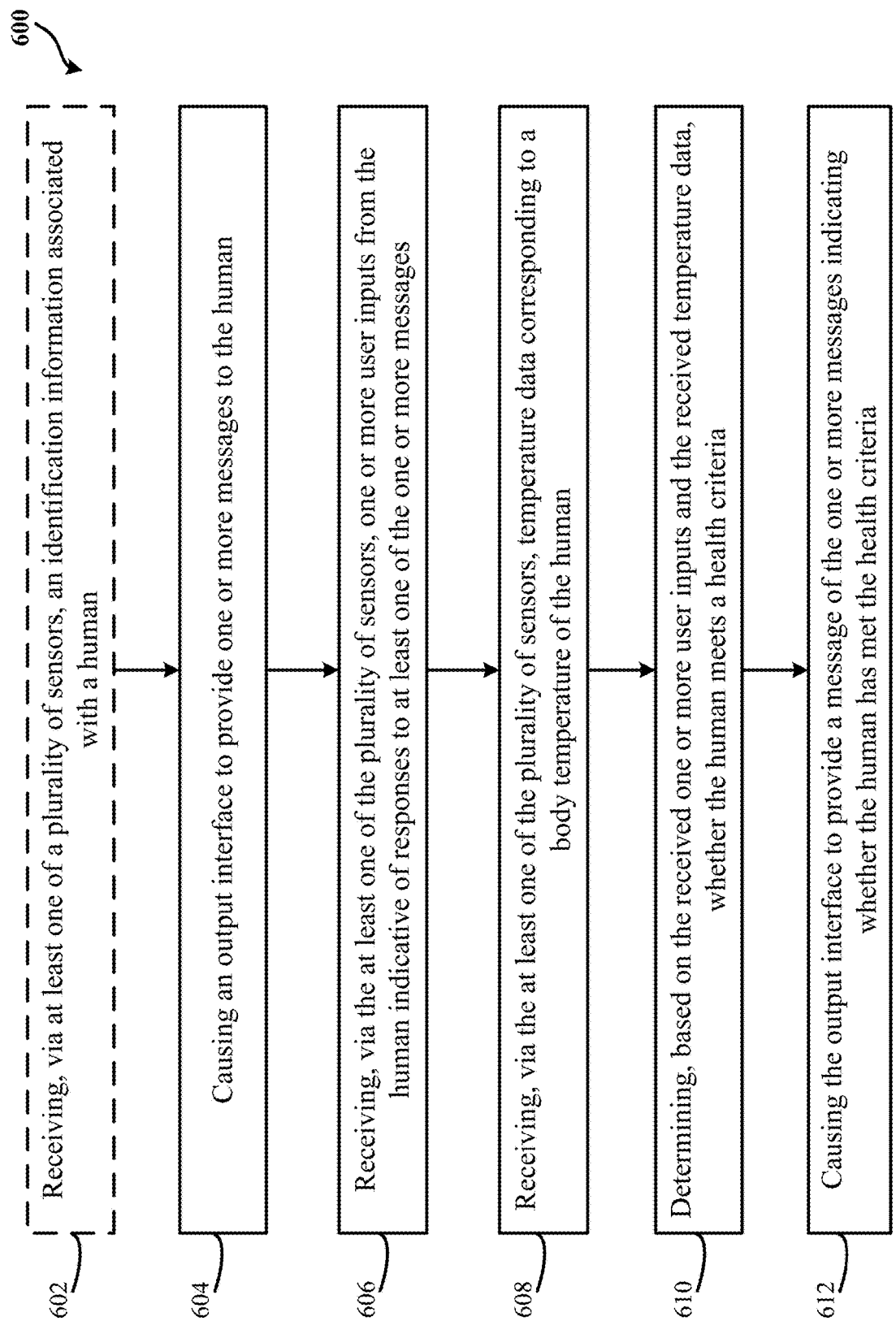
FIG. 6 shows a flow diagram of an exemplary process of touchless screening of a body temperature of a human in accordance with some embodiments.

FIG. 1 illustrates a simplified block diagram of an exemplary system 100 for touchless screening of a health status, e.g., body temperature, of a human 120 in accordance with some embodiments. FIG. 6 shows a flow diagram of an exemplary process and/or method 600 of touchless screening of the health status, e.g., body temperature, of a human in accordance with some embodiments. The system 100 includes a housing 106. The housing 106 may include an output interface 108 that provides one or more messages to a human. A human includes one of an employee of a retail entity, an employee of a vendor of the retail entity, and/or a visitor seeking access to a facility of the retail entity. In some embodiments, some employees may be screened before being allowed access to a facility of the retail entity, while some employees may not need access to a facility in order start a shift and still need to be screened. In some configuration, a visitor may include a customer, a contractor, a delivery agent, and/or the general population that is not an employee of the retail entity. In some configuration, a visitor may include the general population that is not an employee in the facility. In some embodiments, the human is one of a person seeking access to an area, a person seeking approval to perform a task, and/or a person seeking passage. By one approach, the output interface 108 may include a display 202 of FIG. 2, an audio transmitter and receiver, a speaker, and/or a printer. In some embodiments, the system 100 includes a printer distinct from the output interface 108. By one approach, a printer may print a message indicative of whether a human has met a health criteria. For example, one or more messages may include questions regarding the current and/or previous health of the human 120, places the human 120 has traveled, current health symptoms the human 120 may be experiencing, and/or the general health of the human 120. By one approach, those messages output by the output interface 108 are shown in a graphical user interface displaying the messages. A message may include a question, an instructions, and/or an information shown in words and/or visually. As an illustrative non-limiting example, a graphical user interface showing the messages are illustrated FIGS. 8-30. In some embodiments, the graphical user interface displaying the questions associated with determining whether a human 120 has met a health criteria are illustrated in FIGS. 12-15. It is understood by those ordinary skilled in the art that those questions illustrated in FIGS. 12-15 can be asked in a number of sequences or orders different than the sequence as illustrated in FIGS. 12-15.

In some embodiments, the system 100 includes a plurality of sensors 110 coupled to the housing 106. In some embodiments, at least one of the plurality of sensors 110 captures an identification information associated with the human 120. In some embodiments, at least one of the plurality of sensors 110 receives one or more user inputs from the human 120. In some embodiments, at least one of the plurality of sensors 110 detects a body temperature of the human 120. In some embodiments, the plurality of sensors 110 may include at least one of a camera, a barcode scanner, a radio frequency identification (RFID) reader, and a near-field communication (NFC) reader configured to capture an identification badge and/or an identification information. In some embodiments, the plurality of sensors 110 may include at least one of an infrared sensor and a thermal camera. In some embodiments, the plurality of sensors 110 may include at least one of a gesture sensor, an audio sensor, a distance sensor, an ultrasonic sensor, an electronic sensor, and/or a pedal sensor.

In some embodiments, the system 100 includes a control circuit 102 coupled to the output interface 108 and/or the plurality of sensors 110. In some configuration, the control circuit 102 may be coupled to the output interface 108 and/or the plurality of sensors 110 via a communication network 118. In some embodiments, the communication network 118 may include a bus, a wired network, and/or a wireless network, to name a few. In some configuration, the control circuit 102 may, at step 602, receive, via at least one of the plurality of sensors 110, the identification information associated with the human 120. In some configurations, a camera may capture an image of an identification badge or card associated with the human 120. In some configurations, a barcode scanner may scan a barcode in the identification badge. In some configurations, a radio frequency identification (RFID) reader and/or a near-field communication (NFC) reader may capture an identification information programmed in an RFID sensor and/or an NFC sensor embedded in the identification badge. In some embodiments, a camera may capture an image of the human and used image recognition to determine identification of the human. In some embodiments, the control circuit 102 may receive the identification information based in part on the use case, environmental and/or situational context the system 100 is used and/or implemented. For example, the use case and/or the context comprises screening employees before start of a work shift, visitors before authorizing to enter a facility, customers before entering a facility, passengers before entering a plane or before entering customs and immigration. In some embodiments, the use case and/or the context comprises screening and counting people that enter a store, a building, a movie theater, a hospital, a school building, a public transit, an indoor public space, amusement park/ride, event, entertainment venue, to name a few. In some embodiments, the printer described herein prints a sticker, a pass, a ticket, and/or the like granting entry to a facility. In some embodiments, the facility comprises an office space, an access area hosting an event (e.g., holiday meeting), an access area where drivers may gain access to trucks on a parking lot, to name a few. In some embodiments, the facility comprises a store, a stockroom, a distribution center, and a fulfillment center associated with a retail entity.

In a general sense, in some embodiments, the human being screened is one of a person seeking access to an area, a person seeking approval to perform a task, and/or a person seeking passage or entry. Furthermore, it is noted that in some implementations of a health screening process, step 602 is optional in that the context and purpose of the screening does not always require that the identification of the human being screened is obtained. For example, in some embodiments where the human being screened is being screened to assess health fitness to start a work shift and also functions as a time clock, then the identification of the human is needed. However, even in some embodiments involving the screening of employees, it may not always be required to identify the employee being assessed, e.g., if a clock in function is not also occurring by the system and the employee is simply accessing the space or area to then clock in with a separate system. In some embodiments, where the health screening system is used to assess fitness to access an area, such as a movie theater, store, public transportation, it may not be necessary to obtain identification information. For example, it may suffice to determine that the human has paid for entrance for one or more persons and that each of those persons passes the health screening. In such embodiments, it may be more important to screen the health of humans generally without needing to know their identity. Further, such screening applications could consider any applicable privacy laws and/or governmental or jurisdictional restrictions to obtaining identification information or any other image-based or biometric information capture, such as image-based temperature sensing. And some health screening systems may be of a context that consent may needed to for the screened human, and if so, in some embodiments, such consent could be obtained before prompting for and obtaining identification information and/or any other image-based or biometric information capture.

Generally, in some embodiments, the systems and methods described herein can be configured to comply with any applicable privacy requirements which may vary between jurisdictions. For example, before any recording, collection, capturing or processing of user biometric data, a "consent to capture" process may be implemented in some embodiment. In such a process, consent may be obtained in some embodiments, from the human, via a registration process. Part of the registration process may be to ensure compliance with the appropriate privacy laws for the location where the body temperature screening would be performed. In such restricting jurisdictions, in some embodiments, no unauthorized collection or processing of biometric data of individuals occurs via exemplary systems and methods. Once consent is verified, biometric data of the human can be captured, processed and used. Absent verification of consent, in some embodiments, the camera, sensor, and/or other biometric data collection system remains turned off. Once consent is verified, in some embodiments, the camera, sensor and/or other biometric data collection system may be activated or turned on. If any biometric data is inadvertently collected from the human prior to verification of consent, in some embodiments, the collected biometric data is immediately deleted, not having been saved. In some embodiments, any biometric data captured as part of the verification process is handled and stored by a single party at a single location. In some other embodiments where data must be transmitted to an offsite location for verification, certain disclosures prior to consent may be required, and the biometric data is encrypted.

In some embodiments, at step 604, the control circuit 102 causes the output interface 108 to provide one or more messages to a human 120. In some embodiments, at step 606, the control circuit 102 receives, via at least one of the plurality of sensors 110, the one or more user inputs from the human 120 indicative of responses to at least one of the one or more messages. By one approach, the at least one of the plurality of sensors 110 may include a gesture sensor, an audio sensor, a distance sensor, an ultrasonic sensor, an electronic sensor, and a pedal sensor. For example, the one or more user inputs may include a sensor of the plurality of sensors 110 detecting a motion or a hand 214 of the human 120 indicative of a response of the human 120 in response to a message output by the output interface 108. In another example, the one or more user inputs may include a sensor of the plurality of sensors 110 receiving an audio from the human 120 indicative a response to the message. In some embodiments, at step 608, the control circuit 102 receives, via at least one of the plurality of sensors 110, temperature data corresponding to a body temperature of the human 120. For example, the human 120 may present its wrist in front of a sensor of the plurality of sensors 110 in response to a message output by the output interface 108. By one approach, the sensor may include at least one of an infrared sensor and a thermal camera. In some embodiments, the sensors are configured to receive sensed data/inputs without requiring that the human being screened physically contact or touch any surface of the system with their hands or fingers, or in some cases, without any portion of the human's body contacting the screening system. During times of concern over infectious illness and disease, it may be desired to limit the contact of the system and to limit the spread of such illness and disease.

In some embodiments, at step 610, the control circuit 102 determines, based on the received one or more user inputs and/or the received temperature data, whether the human 120 meets a health criteria. It is generally well known to those of ordinary skill in the art how the sensors described herein are capable of detecting and sensing the data they are intended to sense. For example, with respect to sensors detecting body temperature, it is known that such sensors can measure or estimate body temperature, receive measurements or values that correspond to the temperature of the human, or measurements or values useful to calculate the temperature of the human. It is also noted that the factors used to determine whether the human meets the health criteria will depend on the criteria being screened and context and purpose of the health screen and risk. In some embodiments, having a temperature in an acceptable range is an important factor. However, user provided answers to certain questions may prompt a negative health screening despite a normal temperature detection. And in some embodiments, a health screening system may not include a temperature sensing component. For example, it is possible that an abnormal temperature is not a characteristic of an illness or disease of concern and the associated health criteria being screened, such that non-temperature related symptom responses may be provided via the user inputs that can result in a negative screening.

In some embodiments, at step 612, the control circuit 102 causes the output interface 108 to provide a message of one or more messages indicating whether the human 120 has met the health criteria. By one approach, the message may include an authorization to start work when the human 120 has met the health criteria and the human 120 has been determined to be an employee of a retail entity. By another approach, the message may include an authorization to access a facility when the human 120 has met the health criteria and the human 120 has been determined to be an employee of a vendor of the retail entity and/or a visitor (e.g., a customer, a contractor, etc.) of the retail entity. In some embodiments, the system 100 includes a control input/output (I/O) device interface 116 that facilitates communication between the control circuit 102 and one or more devices 126. In some embodiments, the one or more devices 126 may include a printer, a device driver, a latch, an actuator, a light, a door, to name a few. In some embodiments, the one or more devices 126 may include a barrier 126a, such as a door, a turnstile, a gate, an arm gate, and a revolving door, to name a few. For example, the system 100 may be coupled to an automatic door locking mechanism to unlock a door or turnstile for entry, or open a gate, after a determination by the control circuit 102 that the human 120 has met the health criteria. In some embodiments, additional sensors 112 are coupled to the control I/O device interface 116 to provide additional sensed data and/or user input used by the control circuit 102.

In some embodiments, a housing 104 is provided that integrates the control circuit 102, the output interface 108, the sensors 110, the transceiver 114, the control I/O device interface 116 and the communication network 118. In such embodiments, the additional sensors 112 are external to the housing 104. In some embodiments, the housing 106 includes the output interface 108 (e.g., including a display) that enables the output interface 108 to be detachable from the housing 104.

In some embodiments, the control circuit 102 may communicatively couple via a second communication network 124 (e.g., Bluetooth, Wi-Fi, Internet, to name a few of wired and/or wired communication protocols that enable communications between electronic devices) to one or more databases 122 (e.g., memory storage devices, hard disk drives, solid state drives, and/or any electronic devices capable of storing electronic data) and/or one or more servers 128 (e.g., a computer, another control circuits, a smartphone, a processor configured to run a time card software to keep track of hours worked by the employees, to name a few). By one approach, the system 100 includes a transceiver 114 that transmits and/or receives data communicated over the second communication network 124. In some embodiments, the control circuit 102 may cause the output interface 108 to output a barcode and/or a QR code scannable by a user electronic device (e.g., a smartphone) associated with the human 120. In some embodiments, in response to the scanning of the barcode and/or a QR code, the messages (e.g., messages shown in FIGS. 11-15) that would have been output by the output interface 108 are now displayed on the user electronic device (not shown). In such an embodiment, the human 120 may then provide corresponding answers to the messages via the user electronic device. In such an embodiment, the body temperature of the human 120 may be read and/or detected by at least one of the plurality of sensors 110 in the system 100 when prompted by the control circuit 102 via a message shown in the user electronic device.

Figure 2:
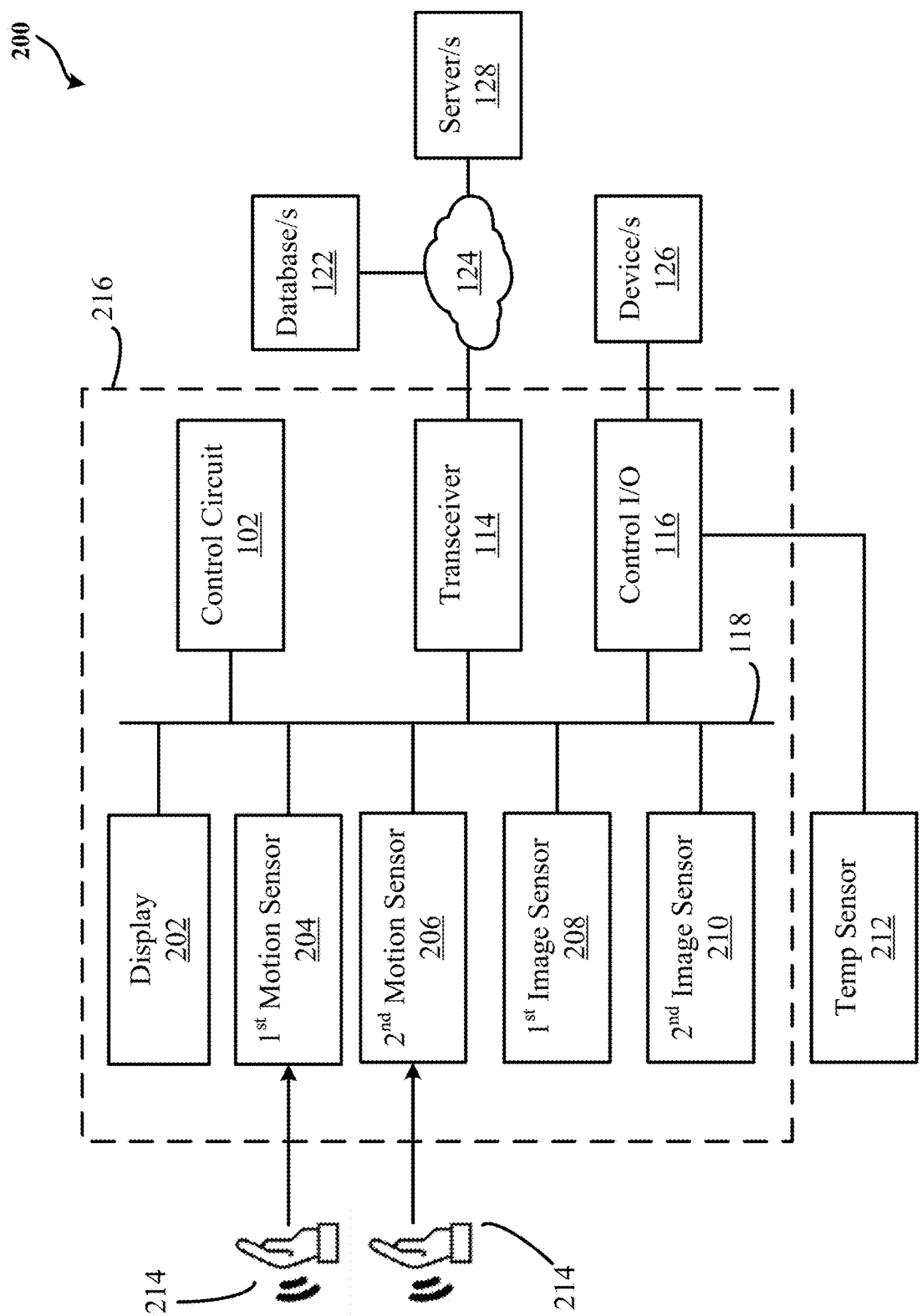
FIG. 2 illustrates a simplified block diagram of an exemplary system for touchless screening of a body temperature of a human in accordance with some embodiments.
Figure 3:
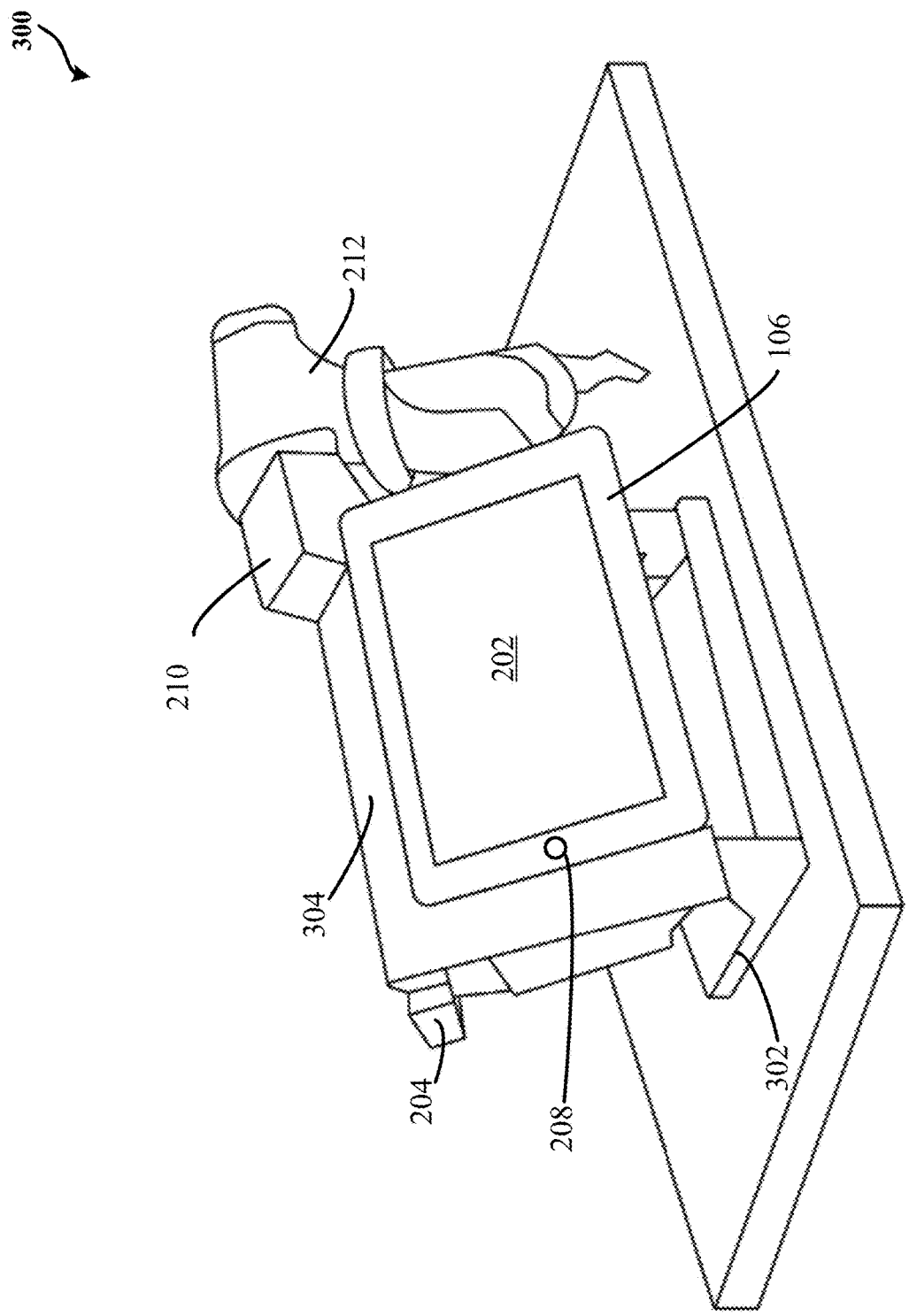
FIG. 3 is a simplified illustration of an exemplary touchless temperature screening system in accordance with some embodiments.

To further illustrate, the embodiments of FIGS. 2 and 3 are also described in connection with the embodiment of FIG. 1. FIG. 2 illustrates a simplified block diagram of an exemplary system 200 for touchless screening of a body temperature of a human in accordance with some embodiments. FIG. 3 is a simplified illustration of an exemplary touchless temperature screening system 300 in accordance with some embodiments. In some embodiments, the system 200 includes a housing 216, and the system 300 includes a housing 304 being an exemplary version of the housing 216. In some embodiments, the housings 204 and 304 include one or more of a display 202, a first motion sensor 204, a second motion sensor 206, a first image sensor 208, a second image sensor 210, the control circuit 102, the transceiver 114, and/or the control I/O device interface 116. In some embodiments, the transceiver 114 may couple with one or more servers 128, the one or more databases 122, and/or the one or more devices 126 via the second communication network 124. In some embodiments, the system 200 may couple to a temperature sensor 212 via the control I/O device interface 116.

In an illustrative non-limiting example, the system 300 of FIG. 3 is a simplified illustration of an exemplary touchless temperature screening system illustrated in the system 200. And in some embodiments, the system 200 is an exemplary illustrative example of the system 100. In some embodiments, the output interface 108 (e.g., the display 202), the plurality of sensors (e.g., a first motion sensor 204, a second motion sensor 206, a first image sensor 208, and a second image sensor 210, and/or the temperature sensor 212), and the control circuit 102 are integrated with the housing. For example, in the system 300 of FIG. 3, the display 202, the first motion sensor 204, the first image sensor 208, and the second image sensor 210 are integrated with the housing 304, whereas the temperature sensor 212 is removably coupled to the housing 304 (e.g., held in a cradle).

In some embodiments, the first motion sensor 204 and the second motion sensor 206 are used to detect motion to activate the screening process and to provide user input responsive to prompts displayed on the display 202. For example, the first motion sensor 204 detects motion from a left hand of the human being screened, and the second motion sensor 206 detects motion from a right hand of the human being screened. In some embodiments, the first image sensor 208 is used to obtain identification information or any other data that needs to be visually captured. corresponding to the human being screened. In some embodiments, the temperature sensor 212 is removably coupled to the housing 304. In some embodiments, the second motion sensor 206 (obstructed by the second image sensor 210 in FIG. 3) is located within a threshold distance to the temperature sensor 212. By one approach, the threshold distance may correspond to about 15 centimeters and/or equivalents thereof. In some embodiments, the second motion sensor 206 detects motion that is used by the control circuit 102 to provide a trigger signal to the temperature sensor 212. For example, when the second motion sensor 206 detects a hand 214/wrist/a body part and/or a motion in front of the second motion sensor 206, the control circuit 102 causes the temperature sensor 212 to start/activate the detection of the body temperature. In some embodiments, the trigger signal is in response to a receipt of a contactless input received/detected by at least one of the first motion sensor 204 and the second motion sensor 206. In some configurations, the contactless input by the human is prompted by a message shown on the display 202. And in some embodiments, the trigger signal is responsive to a signal received via an additional sensor 112 such as shown in FIG. 1 (e.g., see the pedal sensors of FIG. 4).

Once triggered, the temperature sensor 212 takes a measurement. For example, the temperature sensor 212 is activated and the human is directed to position a body part (e.g., wrist) near the temperature sensor 212. In some embodiments, the sensed temperature may be directly coupled to the control circuit 102 via the control I/O device interface 116. In some embodiments, the second image sensor 210 is oriented to view an output display screen (not shown) of the temperature sensor 212 to capture an image of the temperature sensor 212 output. For example, many commercial temperature sensors include an LCD (liquid crystal display) or other suitable visual display that displays the read temperature. By having the second image sensor 210 proximate to and directed to view the output display of the temperature sensor 212, the output of the temperature sensor 212 can be input to the control circuit 102 indirectly via the second image sensor 210. Thus, in some embodiments, the control circuit 102 can receive temperature data corresponding to the body temperature directly via electrical connection (via the control I/O device interface 116) to the temperature sensor 212 and/or indirectly via the second image sensor 210. In some embodiments, the control circuit 102 receives the temperature data and compares the any directly received temperature data with the temperature value read/captured by the second image sensor 210 from the display screen of the temperature sensor 212. By one approach, the comparison of the temperature value read/captured by the second image sensor 210 with the temperature data directly received via the temperature sensor 212 provides for a system check to determine the reliability of the body temperature received by the control circuit 102. In some embodiments, the system 200 includes a portable base 302.

In some embodiments, and as shown in the exemplary system 300 pf FIG. 3, the housing 304 is mounted on the portable base 302 that enables the housing 304 to be movable from one place to another place, and thereby, making the systems described herein portable and capable to be conveniently placed anywhere the screening of the body temperature is needed. In some embodiments, the housing 106 of FIG. 1 includes the display 202 enables the display 202 to be detachable from the housing 104. In some embodiments, the system 300 of FIG. 3 is touchless or contactless in that there is no direct or indirect physical contact from a human in order to operate the system 300.

Figure 4:
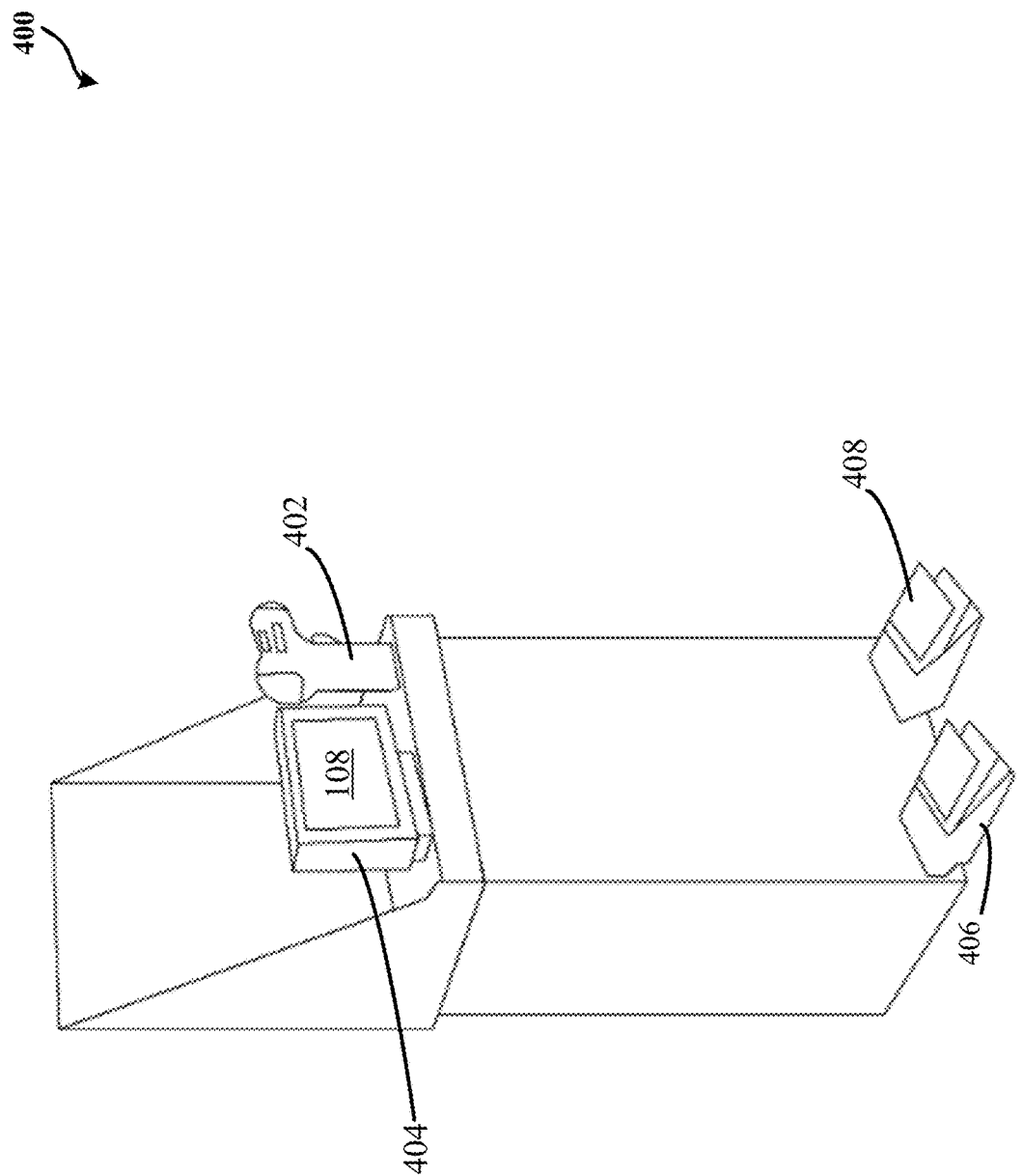
FIG. 4 is a simplified illustration of an exemplary touchless temperature screening system in accordance with some embodiments.
Figure 5:
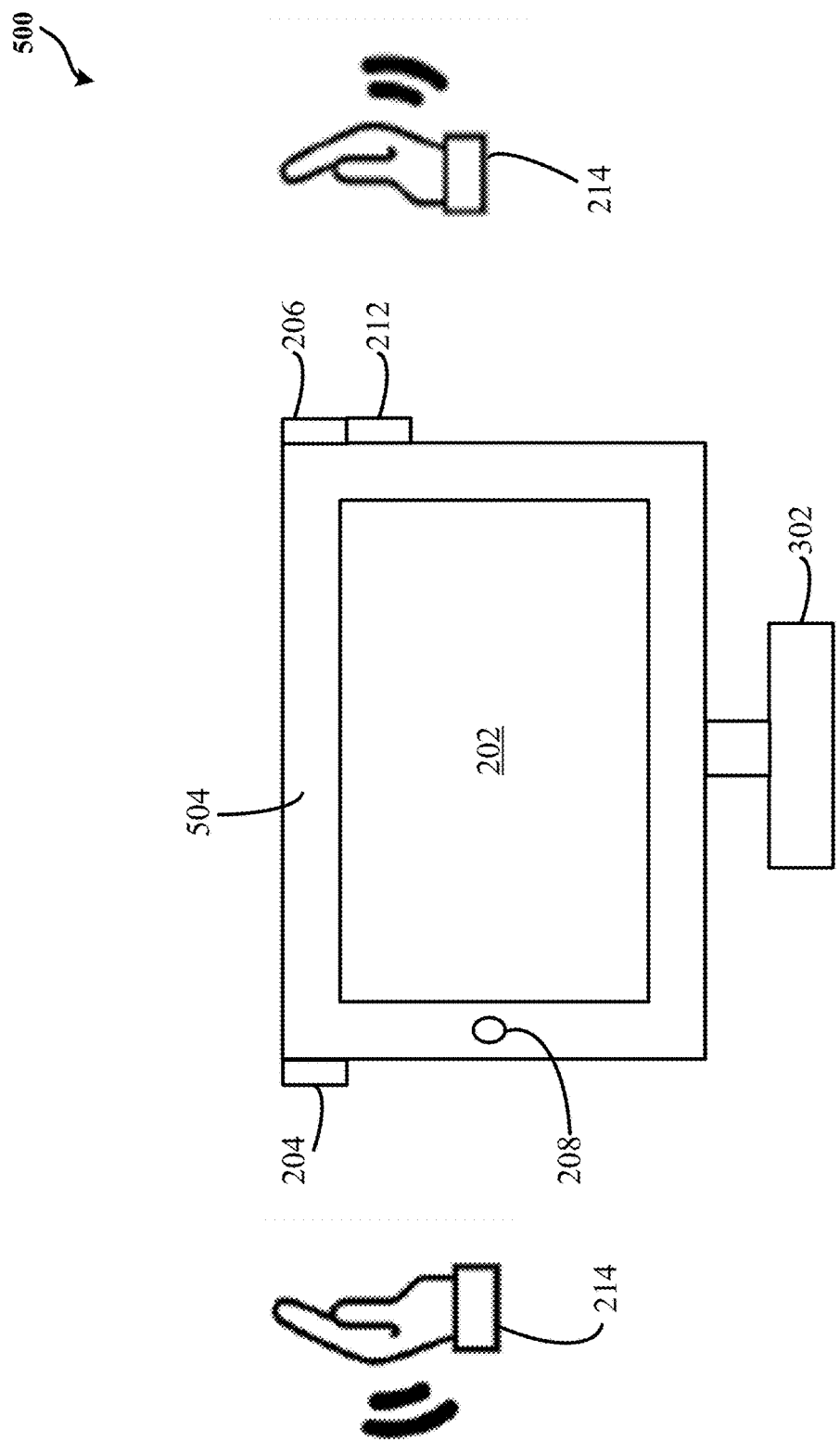
FIG. 5 is a simplified illustration of an exemplary touchless temperature screening system in accordance with some embodiments.

To further illustrate, the embodiments of FIGS. 4 and 5 are also described with the embodiments of FIGS. 1-3. FIG. 4 is a simplified illustration of an exemplary touchless temperature screening system 400 having a housing 404 in accordance with some embodiments. In some embodiments, the system 400 is an illustrative non-limiting exemplary example of the system 100 and/or the system 200. In some embodiments, in the system 400, a temperature sensor 402 may correspond to the temperature sensor 212 of FIG. 2. In some embodiments, in the system 400, one or more pedal sensors 406, 408 may correspond to the additional sensor/s 112 of FIG. 1. In some embodiments, the one or more pedal sensors 406, 408 receive the one or more user inputs from the human 120 where the inputs are indicative of responses to one or more messages provided by the output interface 108. In some embodiments, the one or more pedal sensors 406, 408 may be additional to the first motion sensor 204 and the second motion sensor 206 in FIG. 2 to receive the one or more user inputs from the human 120 where the inputs are indicative of responses to one or more messages provided by the output interface 108. In some embodiments, the one or more pedal sensors 406, 408 may be an alternative to the first motion sensor 204 and the second motion sensor 206 in FIG. 2 to receiving the one or more user inputs from the human 120. The system 400 illustrates the system 100 and/or the system 200 in a kiosk-type environment. In some embodiments, the system 400 illustrates the temperature sensor 402 that is separate and distinct from the housing 404. In some embodiments, the temperature sensor 402 of FIG. 4 may be integrated with the housing 404. Likewise the temperature sensors described herein (such as temperature sensor 212) may be integrated into with the system housings 104, 216, 304. Alternatively, the temperature sensors described herein (such as at least one of sensors 110, temperature sensor 212, temperature sensor 402) may be configured to be removably detachable from the respective housing 104, 204, 304, 404.

In the embodiments of FIG. 4, it is understood that by operation of the pedals 406 and 408 by the foot of a human, the housing 404, the output interface 108 and temperature sensor 402 are touchless or contactless in that there is no direct or indirect human contact with these components. And, the system 400 as a whole is touchless or contactless in that there is no direct or indirect human contact by the human's hand and/or finger, i.e., only the shoe or footwear of the user directly contacts the system 400.

To further illustrate, the embodiments of FIGS. 5 and 8-30 are described. FIG. 5 is a simplified illustration of an exemplary touchless temperature screening system 500 in accordance with some embodiments. In some embodiments, the system 500 is an illustrative non-limiting exemplary example of the system 100 and/or the system 200. As such, descriptions provided herein with reference to system 500 is equally applicable to other systems described herein, such as systems 100, 200 and 300. FIGS. 8-30 are illustrative graphical user interfaces showing exemplary steps in an exemplary process of touchless screening of a body temperature of a human in accordance with some embodiments. In some embodiments, the control circuit 102 of the systems 100, 200 and/or 300 causes one or more of the graphical user interfaces shown in FIGS. 8-30 to be displayed on the output interface 108 and/or the display 202.

In some embodiments, the system 500 includes the display 202, the first motion sensor 204, the second motion sensor 206, the temperature sensor 212, and the first image sensor 208. In some embodiments, the display 202, the first motion sensor 204, the second motion sensor 206, the temperature sensor 212, and the first image sensor 208 are integrated with the housing 504. In some embodiments, the system 500 includes the portable base 302. In some embodiments, the housing 504 is mounted in the portable base 302. In some embodiments, the first motion sensor 204, the second motion sensor 206, the temperature sensor 212, and the first image sensor 208 are configured to operate and/or perform a detection and/or capture of data without physical contact from a human 120. As an illustrative non-limiting example, an operation and/or an application in the system 500 may be initiated based on a detected hand motion (e.g., a waving of a hand 214, a swiping motion of a hand 214, a chopping motion of a hand 214, and/or placing a hand 214 in front of either motion sensor 204, 206, to name a few). For example, the human 120 may perform a hand motion 214 in front and/or in close proximity to at least one of the first motion sensor 204 and the second motion sensor 206. Alternatively, or in addition to, the system 500 may be initiated based on an audio/voice command received from the human 120, e.g., via a microphone or other audio sensor. In some embodiments, in response to receiving and/or detecting the hand motion 214, the control circuit 102 causes the graphical user interface of the display 202 to display a graphical user interface 800 of FIG. 8. The graphical user interface 800 instructs the human 120 to make a selection by performing a hand motion in accordance to the status of the human 120 relative to a retail entity (e.g., visiting vendor and/or home office associates on the left side and club associates on the right side).

In some embodiments, an affirmative or a yes response to any of the one or more messages corresponds to the hand 214 moving across or in front of a first one of the plurality of sensors 110 (e.g., motion sensor 204) configured to receive the one or more user inputs in accordance with the instruction, prompt or message shown on the graphical user interface on the display 202. In some embodiments, a negative or a no response to any of the one or more messages corresponds to the hand 214 moving across or in front of a second one of the plurality of sensors (e.g., motion sensor 204) configured to receive the one or more user inputs in accordance with the instruction, prompt or message shown on the graphical user interface on the display 202.

Figure 9:
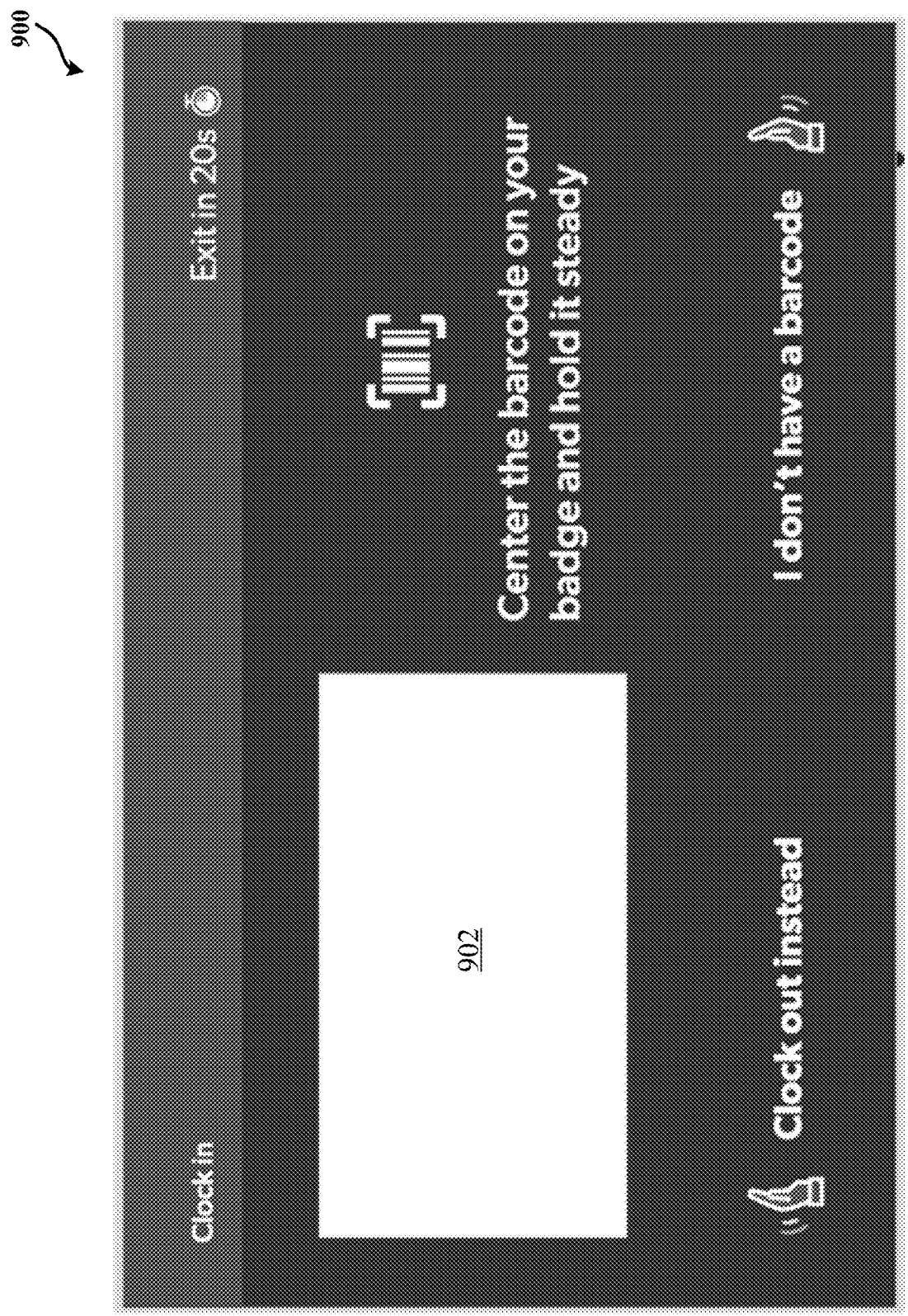

In some embodiments, in response to the selection of the club associates (hand motion at the second motion sensor 206), the control circuit 102 causes the graphical user interface of the display 202 to display a graphical user interface 900 of FIG. 9. In the graphical user interface 900, the control circuit 102 is instructing the human 120 to scan a barcode associated with the human 120. In some embodiments, the scanning of the barcode by the first image sensor 208, causes the control circuit 102 to determine the corresponding time the barcode was scanned. By one approach, the control circuit 102 determines that the corresponding time is a time data corresponding to the human 120 clocking in to start a work shift. In some embodiments, a window portion 902 of the graphical user interface 900 displays the view as seen by the first image sensor 208 to assist the human in aligning the identification card, badge or information.

Figure 10:
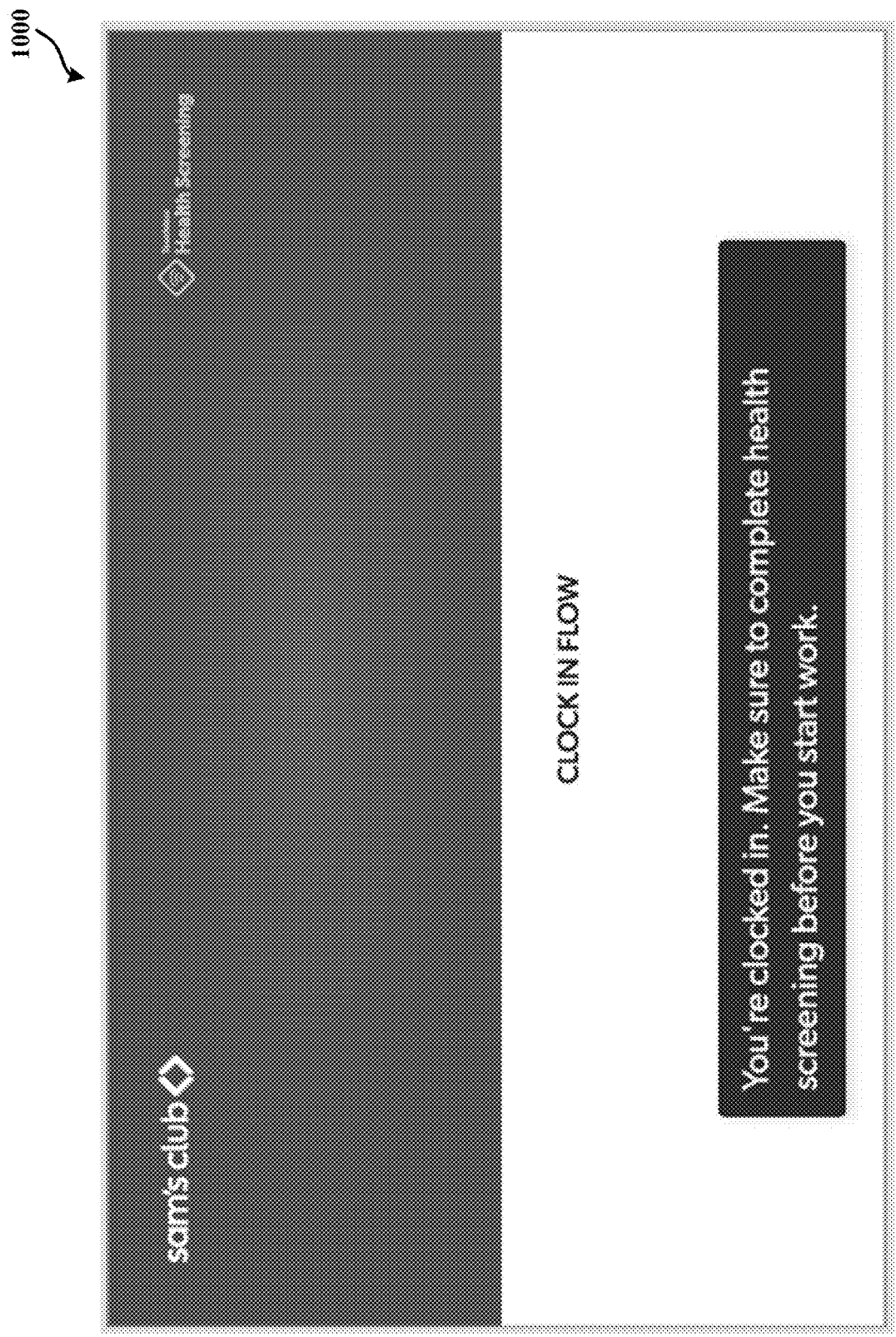
Figure 11:
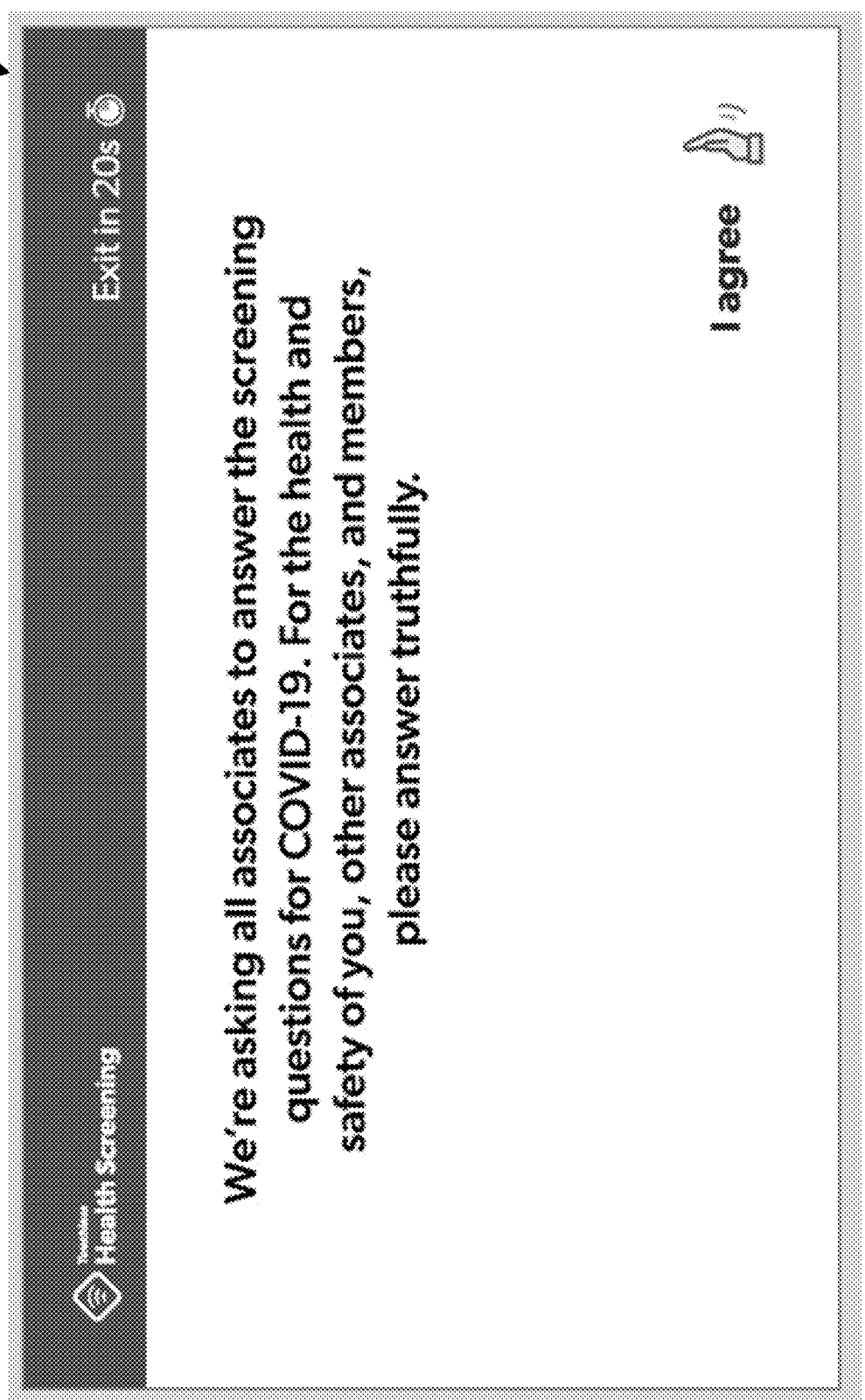
Figure 13:
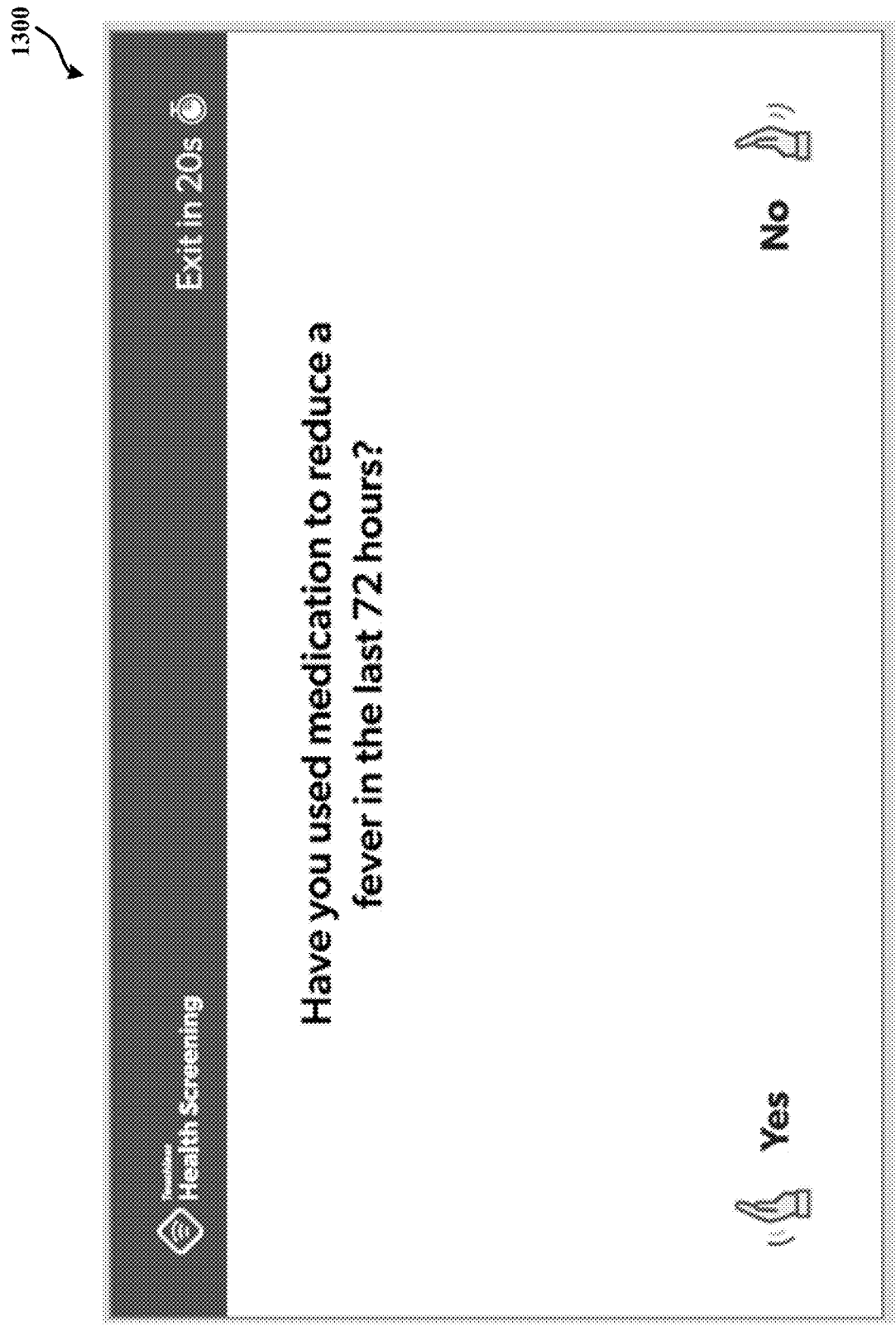
Figure 14:
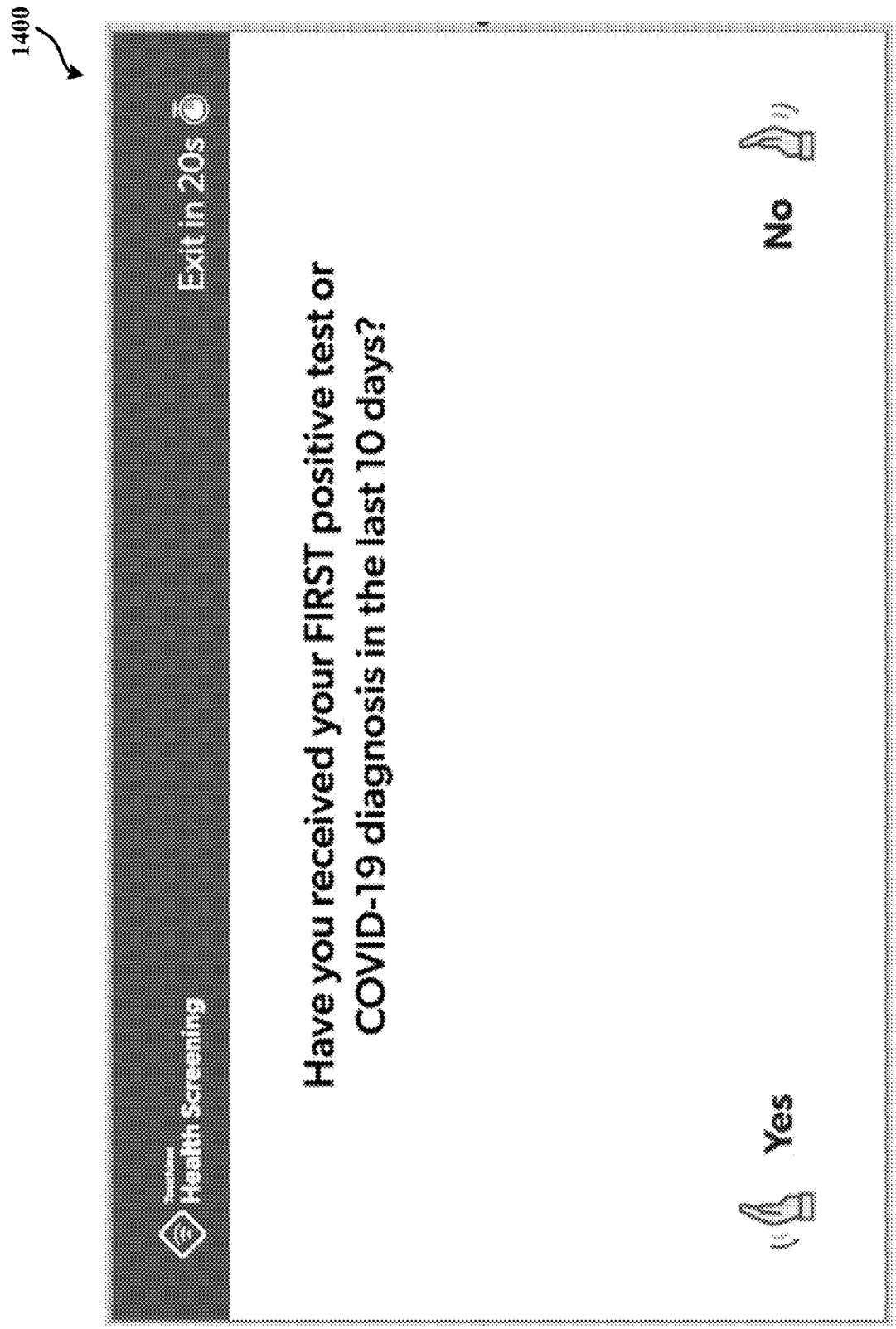
Figure 15:
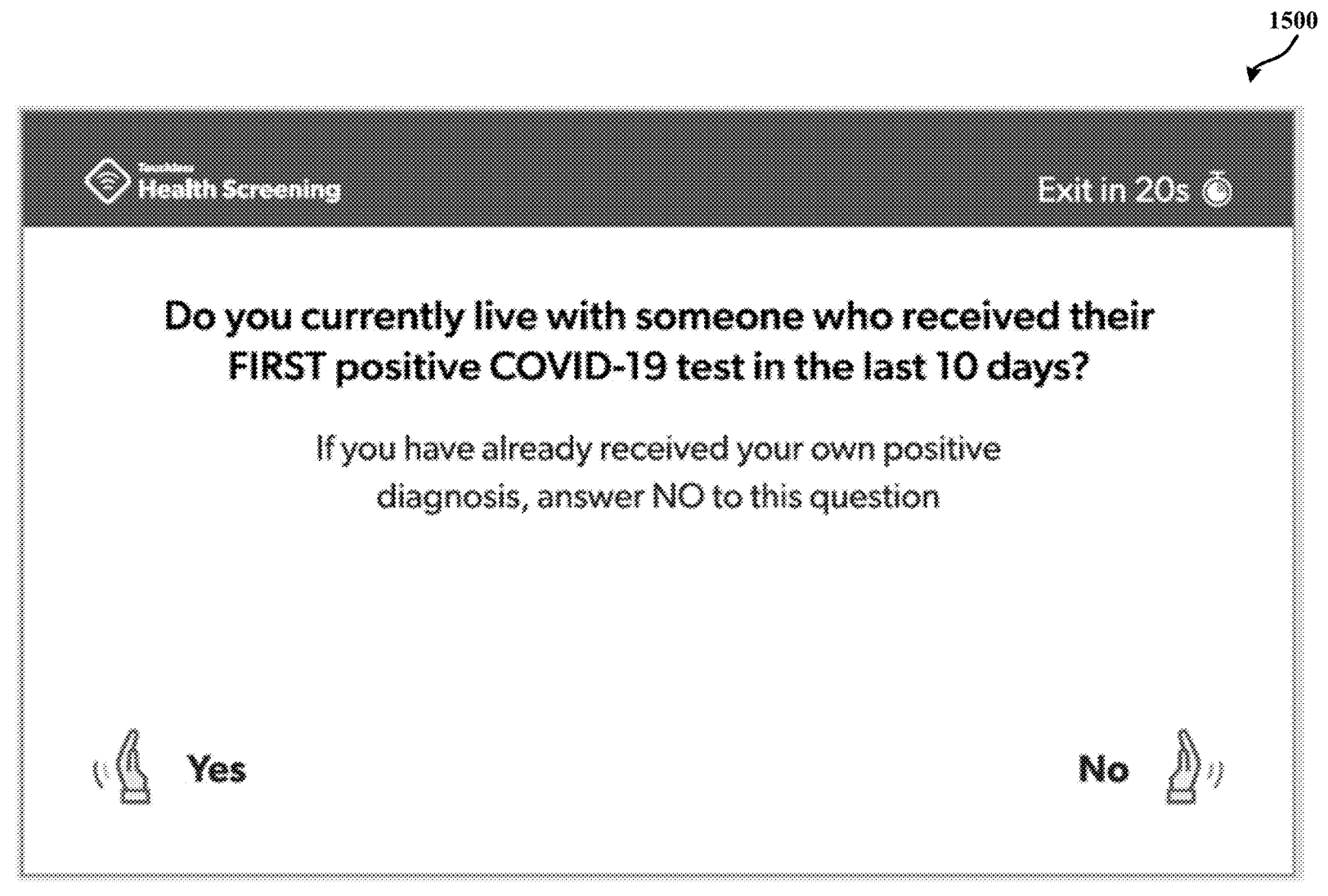

In some embodiments, in response to the scanning of the barcode as instructed in the graphical user interface 900 of FIG. 9, the control circuit 102 causes the graphical user interface of the display 202 to display a graphical user interface 1000 of FIG. 10. In some embodiments, the graphical user interface shown in the display 202 may change to one or more graphical user interfaces shown in FIGS. 11-15 (e.g., a graphical user interface 1100 of FIG. 11, a graphical user interface 1200 of FIG. 12, a graphical user interface 1300 of FIG. 13, a graphical user interface 1400 of FIG. 14, and/or a graphical user interface 1500 of FIG. 15) after a period of time (e.g., a second or a fraction of a second, etc.). As illustrated, the graphical user interface 1100 informs the human that they will be provided a series of screening questions as part of the screening process and provides the option to proceed. And as illustrated in each of the example graphical user interfaces 1200, 1300, 1400, and 1500 of FIGS. 12-15, the human is asked a specific question useful at least in part to assessing the health status of the human being screened. It is understood that the specific questions asked will be specific to the nature of health inquiry and/or circumstances of the specific health concern/s. The illustrated interfaces pose questions specific to an example health concern regarding assessing risk relating to COVID-19, which at the time of filing, is at the root of a current pandemic. In some embodiments, an affirmative or a yes response to any of the one or more messages shown in FIGS. 12-15 corresponds to the hand 214 moving across or in front of the first motion sensor 204. In some embodiments, a negative or a no response to any of the one or more messages shown in FIGS. 12-15 corresponds to the hand 214 moving across or in front of the second motion sensor 206.

Figure 16:
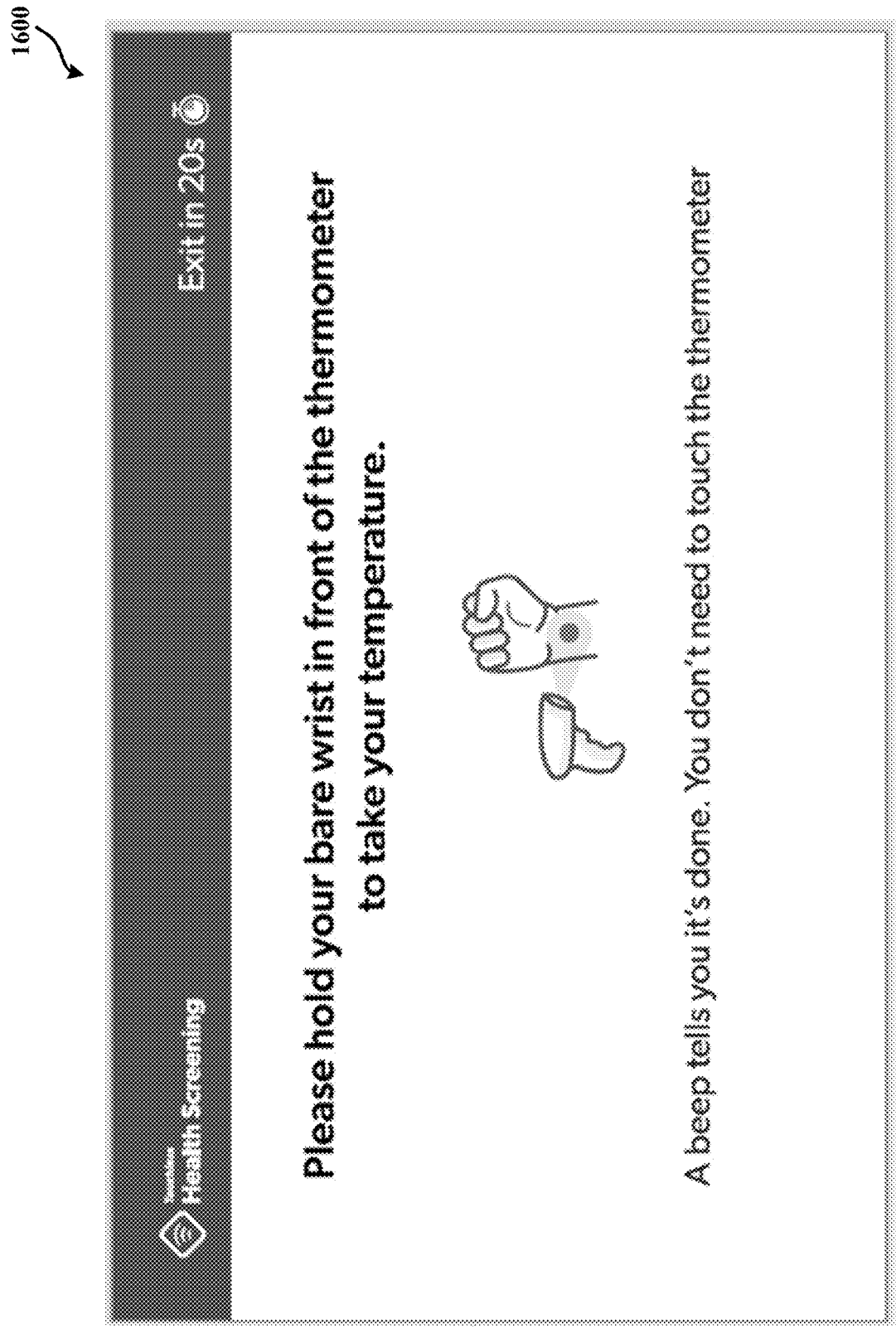
Figure 17:
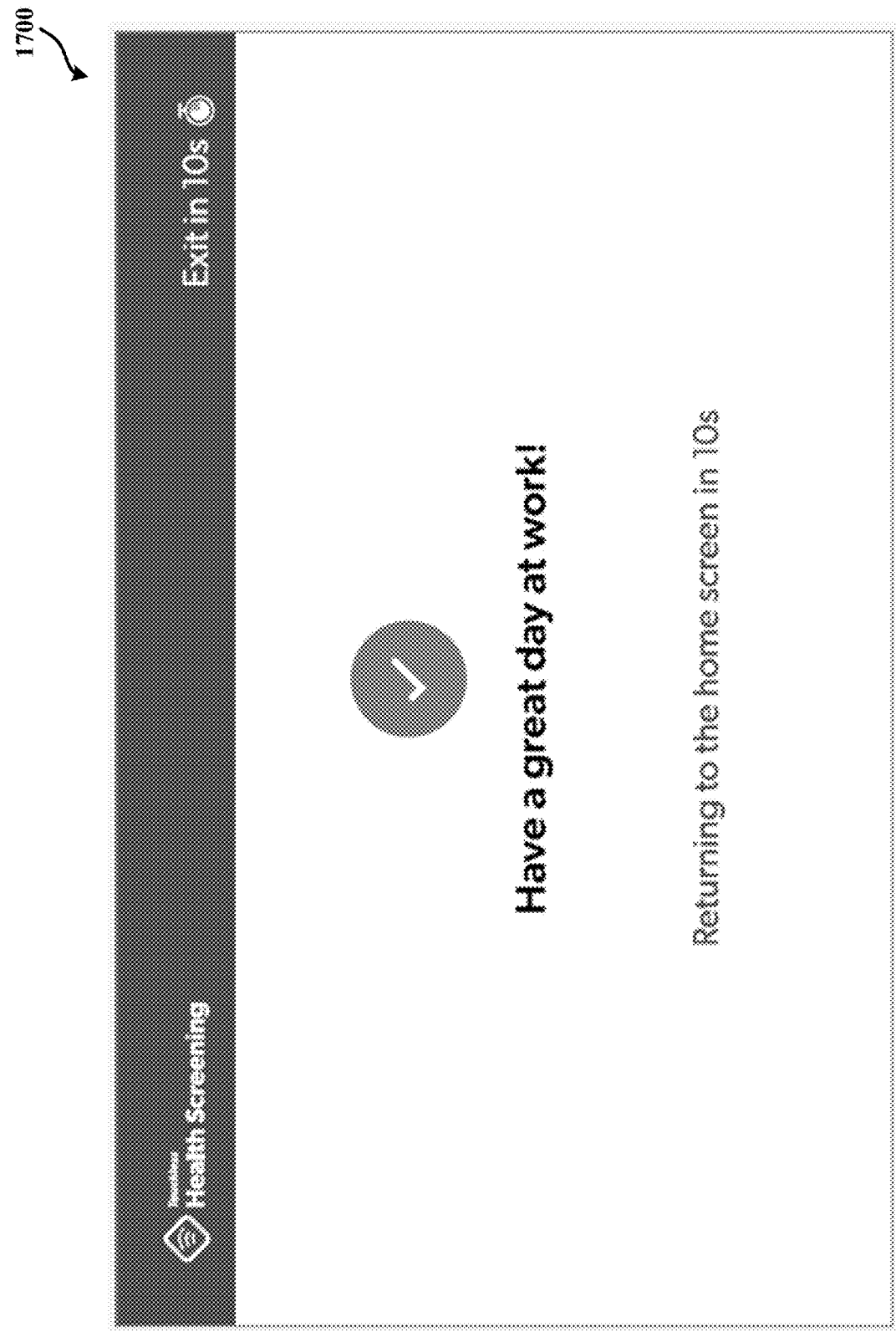
Figure 18:
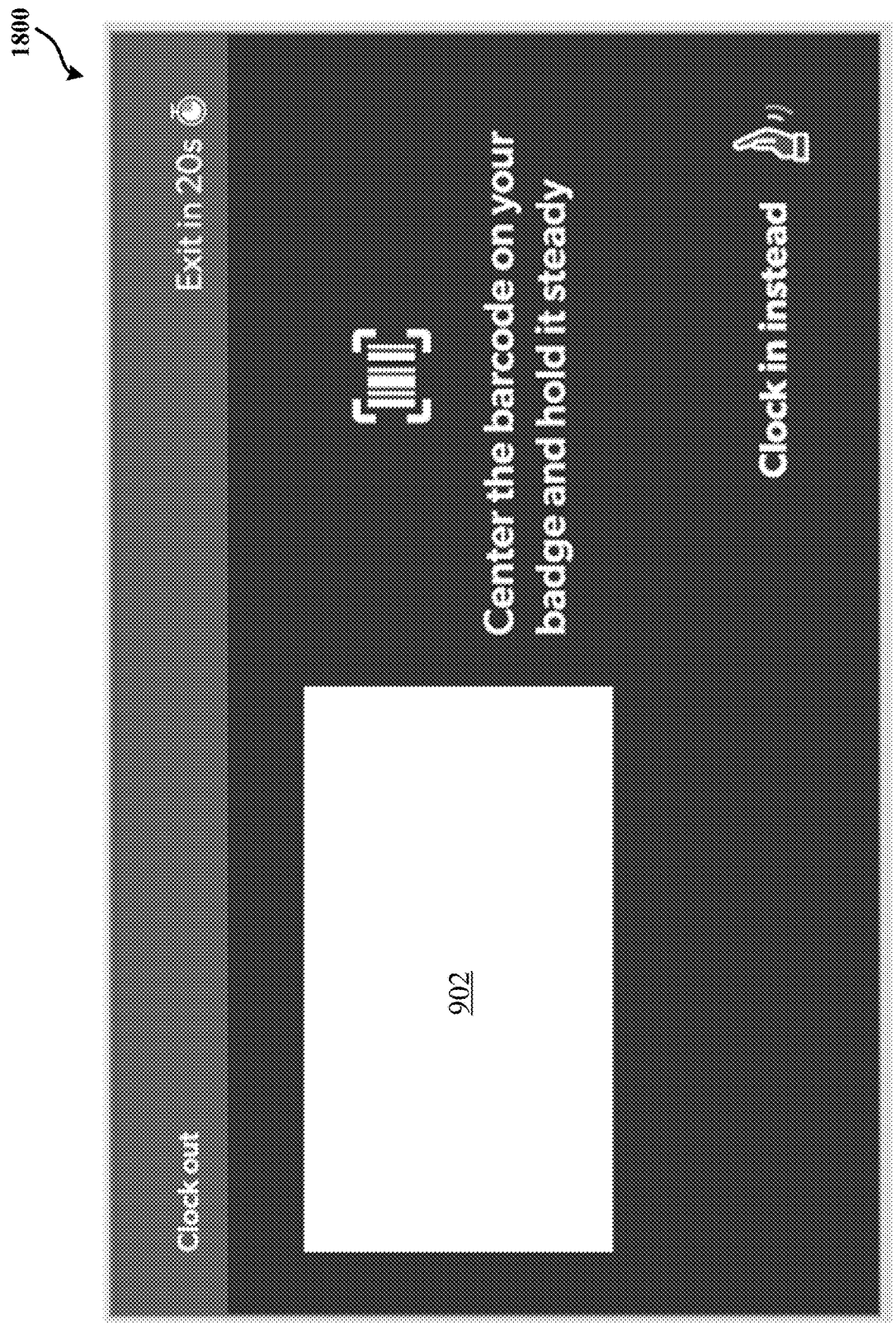
Figure 19:
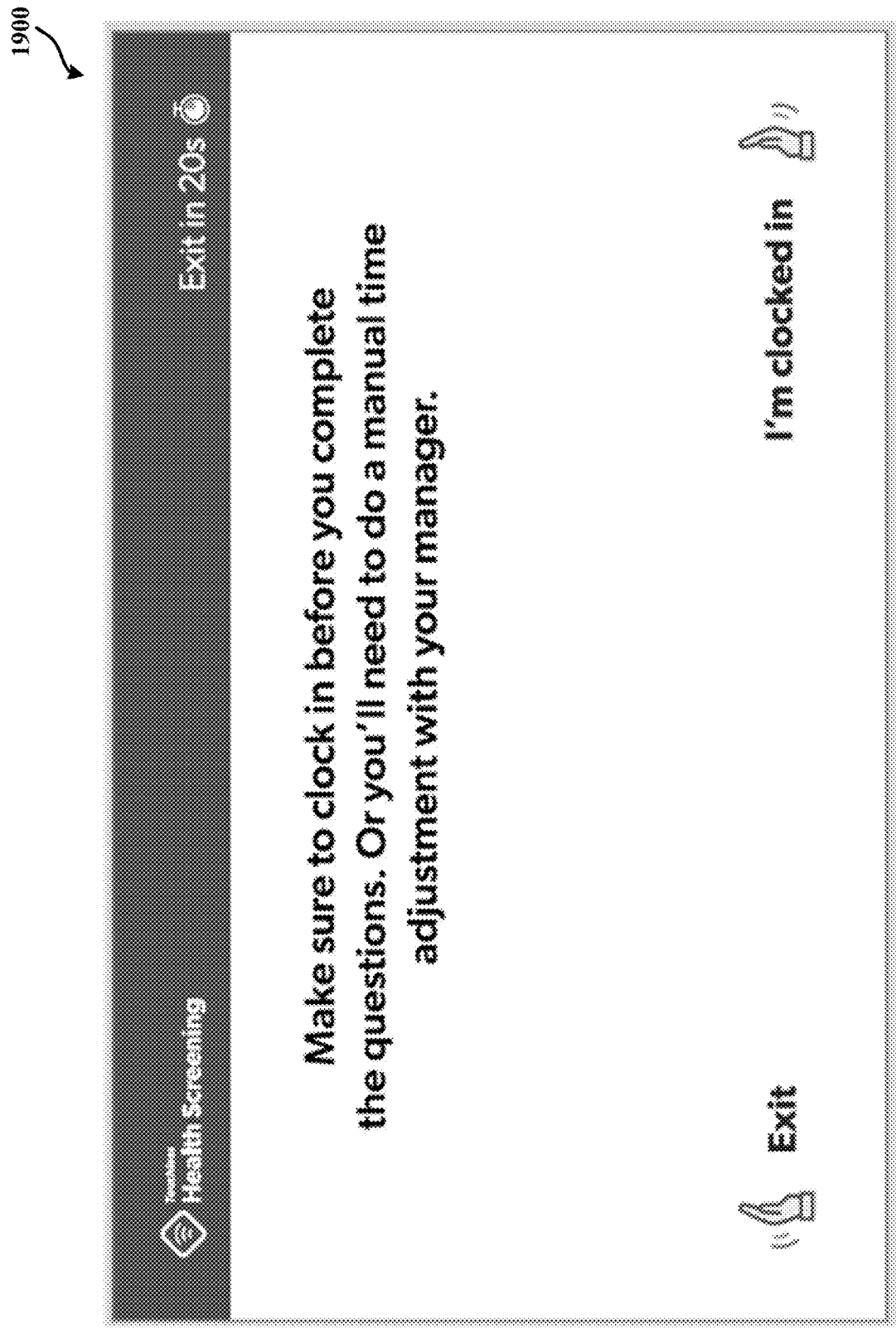
Figure 20:
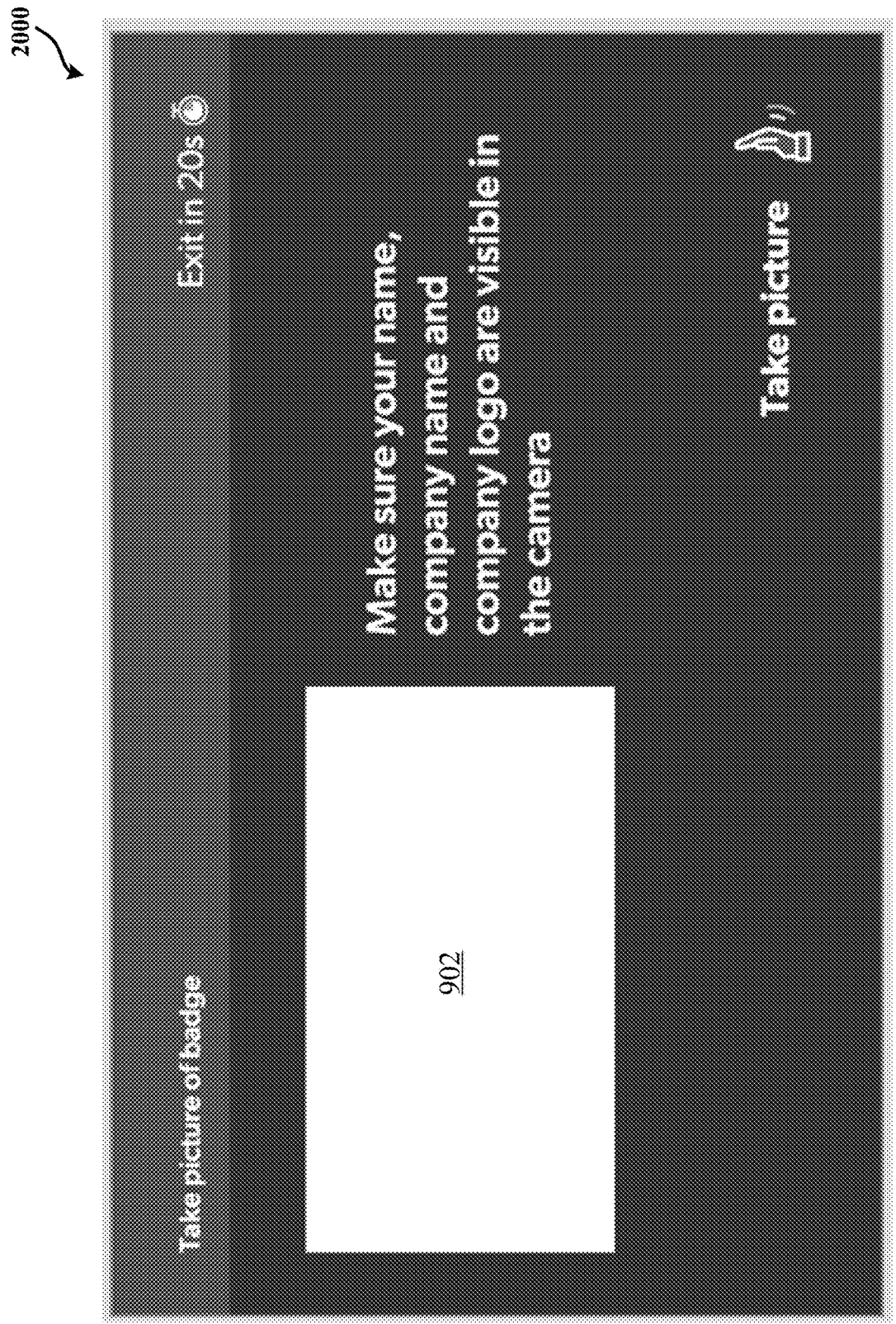
Figure 21:
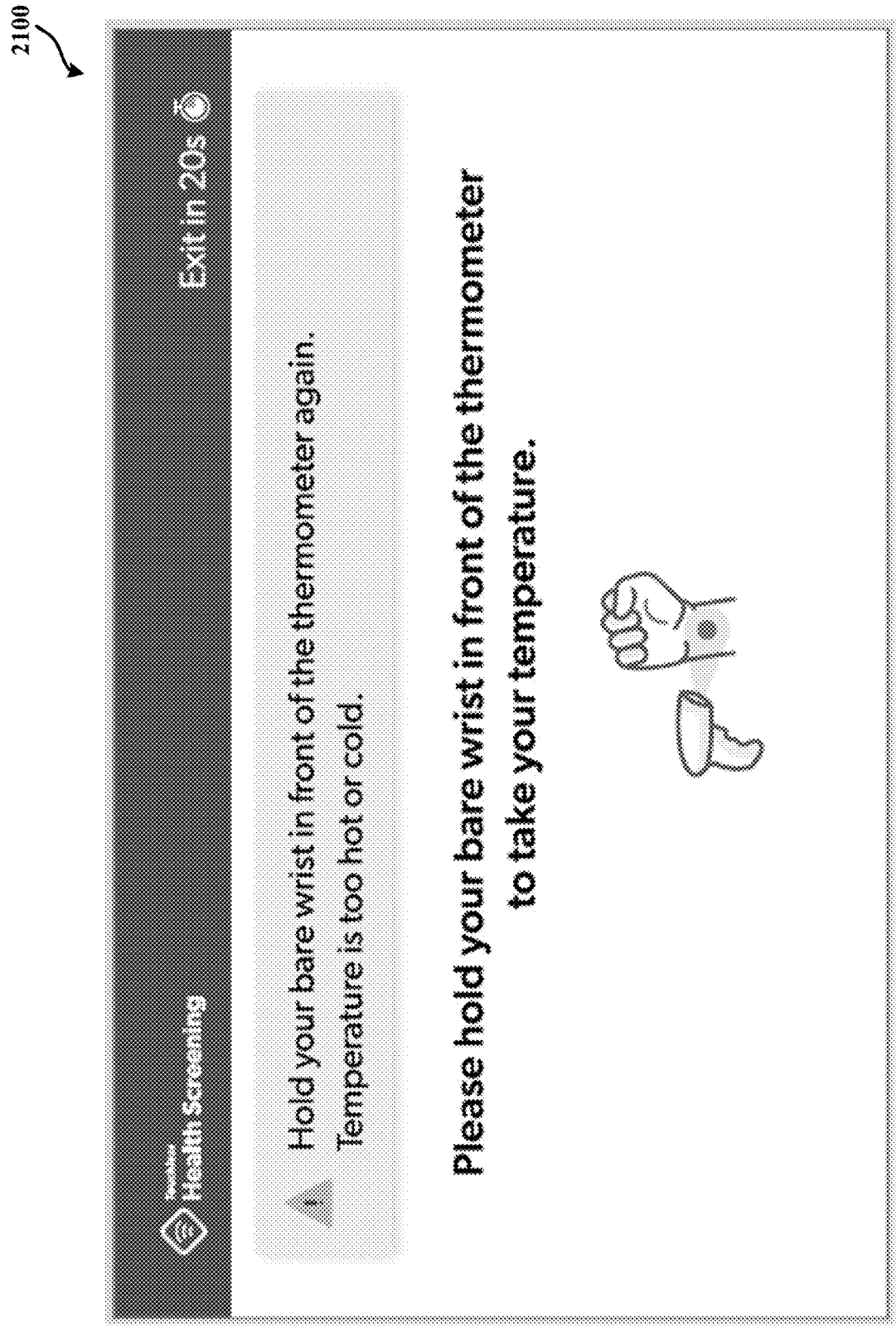
Figure 22:
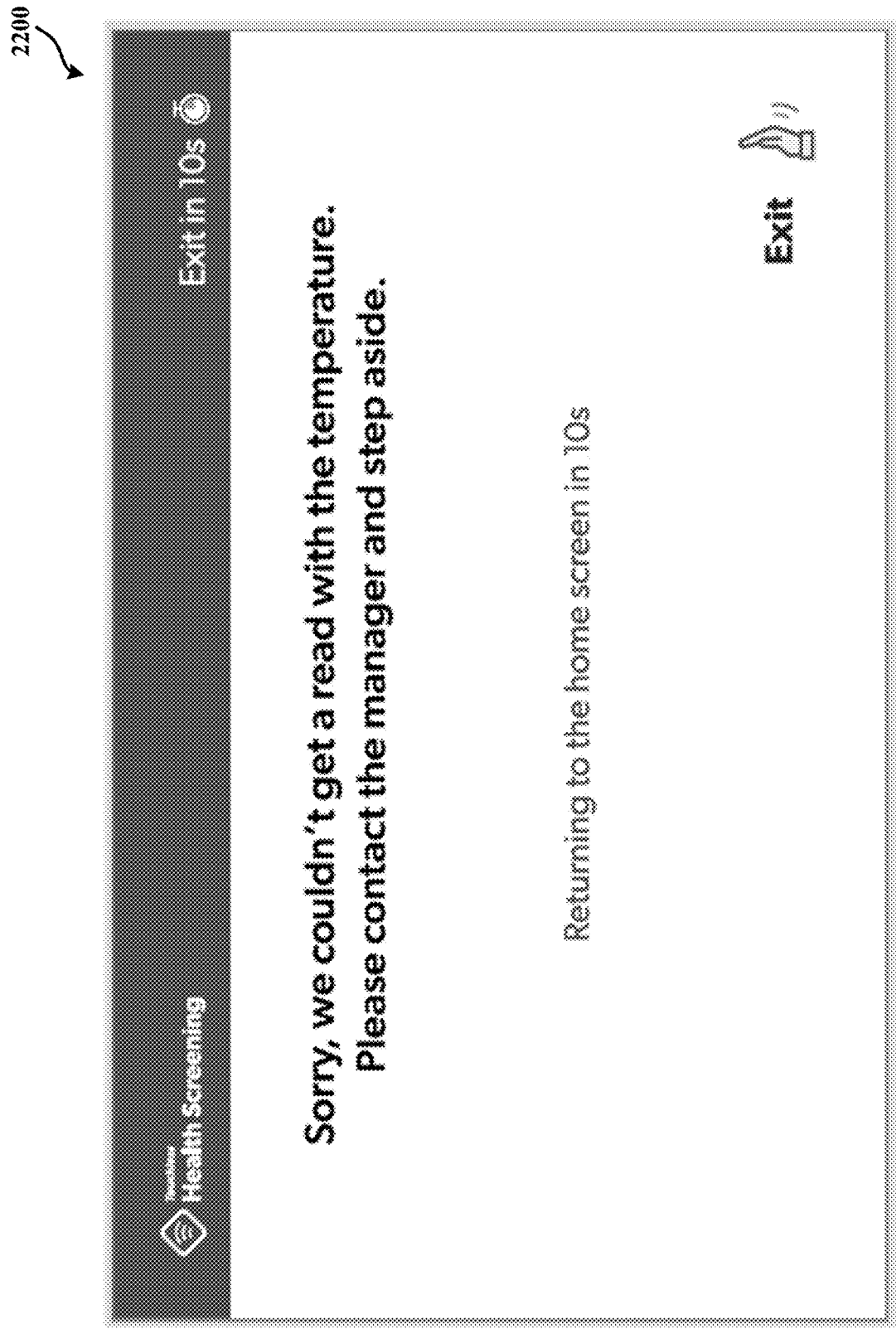

In some embodiments, after another period of time (e.g., a second or a fraction of a second, etc.) the graphical user interface shown in the display 202 may change from displaying one or more graphical user interfaces shown in FIGS. 11-15 to a graphical user interface 1600 of FIG. 16 instructing the human 120 to have their temperature sensed, e.g., by holding the wrist in front of the temperature sensor 212. In some embodiments, the control circuit 102 may cause an alarm circuit or audio output such as a speaker (not shown) to emit a single audible beep sound when the control circuit 102 determines that the read and/or detected body temperature is within a predetermined temperature range. In some embodiments, the control circuit 102 may cause the alarm circuit or audio output to emit three audible beep sound when the control circuit 102 determines that the read and/or detected body temperature is outside the predetermined temperature range. In some embodiments, the control circuit 102 may determine and/or obtain the body temperature detected by the temperature sensor 212 in response to receiving, via a microphone coupled to the control circuit 102, an audio signal triggered by the temperature sensor 212. In some embodiments, the control circuit 102 may cause the temperature sensor 212 to read/detect the body temperature a predetermined number of times (e.g., two, three, four, to name a few) before the control circuit 102 determines that the human 120 has failed to meet the health criteria. For example, after the human 120 failing to initially get a reading of a body temperature that is within the predetermined temperature range, the control circuit 102 may cause the graphical user interface of the display 202 to display a graphical user interface 2100 of FIG. 21 instructing the human 120 to hold the wrist in front of the temperature sensor 212 one or more times. In some embodiments, in response to failing to detect and/or determine to read a body temperature that is within the predetermined temperature range, the control circuit 102 may cause the graphical user interface of the display 202 to display a graphical user interface 2200 of FIG. 22 instructing the human 120 to step aside and contact a manager. Alternatively, in response to the control circuit 102 detecting and/or determining a body temperature that is within the predetermined temperature range, the control circuit 102 may cause the graphical user interface of the display 202 to display a graphical user interface 1700 of FIG. 17 authorizing the human 120 to start the work shift. It is understood that the context of the output display message that the user has passed screening will change based on the nature of the screening taking place, e.g., if the screening is for the purpose of granting access to an area, the message may indicate that the human has passed screening and may continue.

In some embodiments, the control circuit 102 may determine that the human 120 has failed to meet the health criteria when the human 120 has responded an affirmative or yes response in at least one of the questions in FIGS. 12-15. In some embodiments, in response to the determination that the human 120 failed to meet the health criteria, the control circuit 102 may cause the graphical user interface of the display 202 to display a graphical user interface 2300 of FIG. 23 instructing the human 120 that he/she did not meet the health criteria and the subsequent actions that the human 120 can do. In some embodiments, when the human 120 fails to meet the health criteria, the control circuit 102 may transmit via the second communication network 124 a message to a manager and/or supervisor indicating that the human 120 has failed to meet the health criteria and/or an assistance is requested. It is also noted that the decision whether the human has passed the screening can be dependent on the situation and answers received. For example, a human having an acceptable temperature may not pass the screen if the human has answered yes to one or more of the questions. For example, a yes answer to graphical user interfaces 1400 and/or 1500 may result in not passing the screening despite a normal temperature detection.

Figure 23:
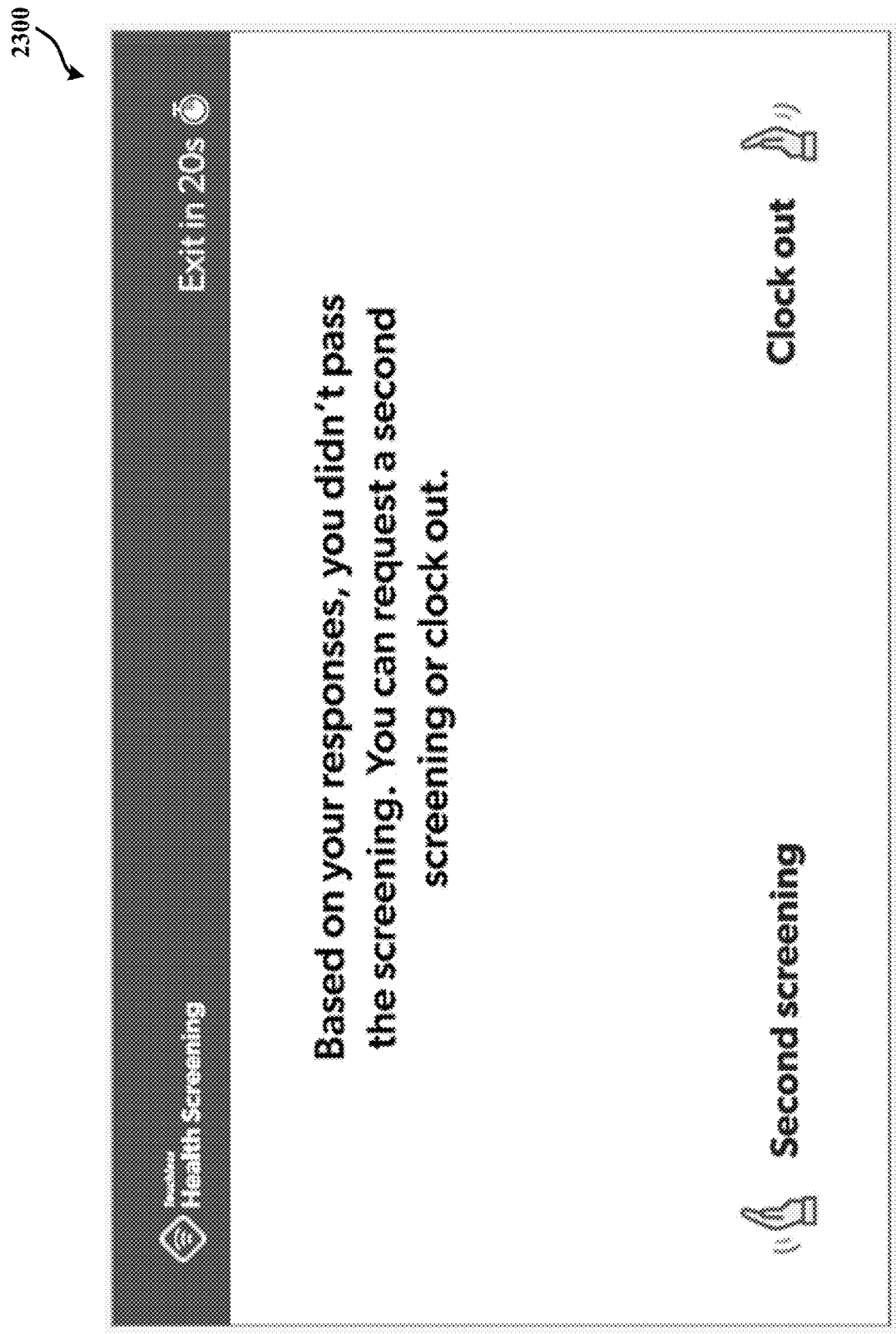
Figure 24:
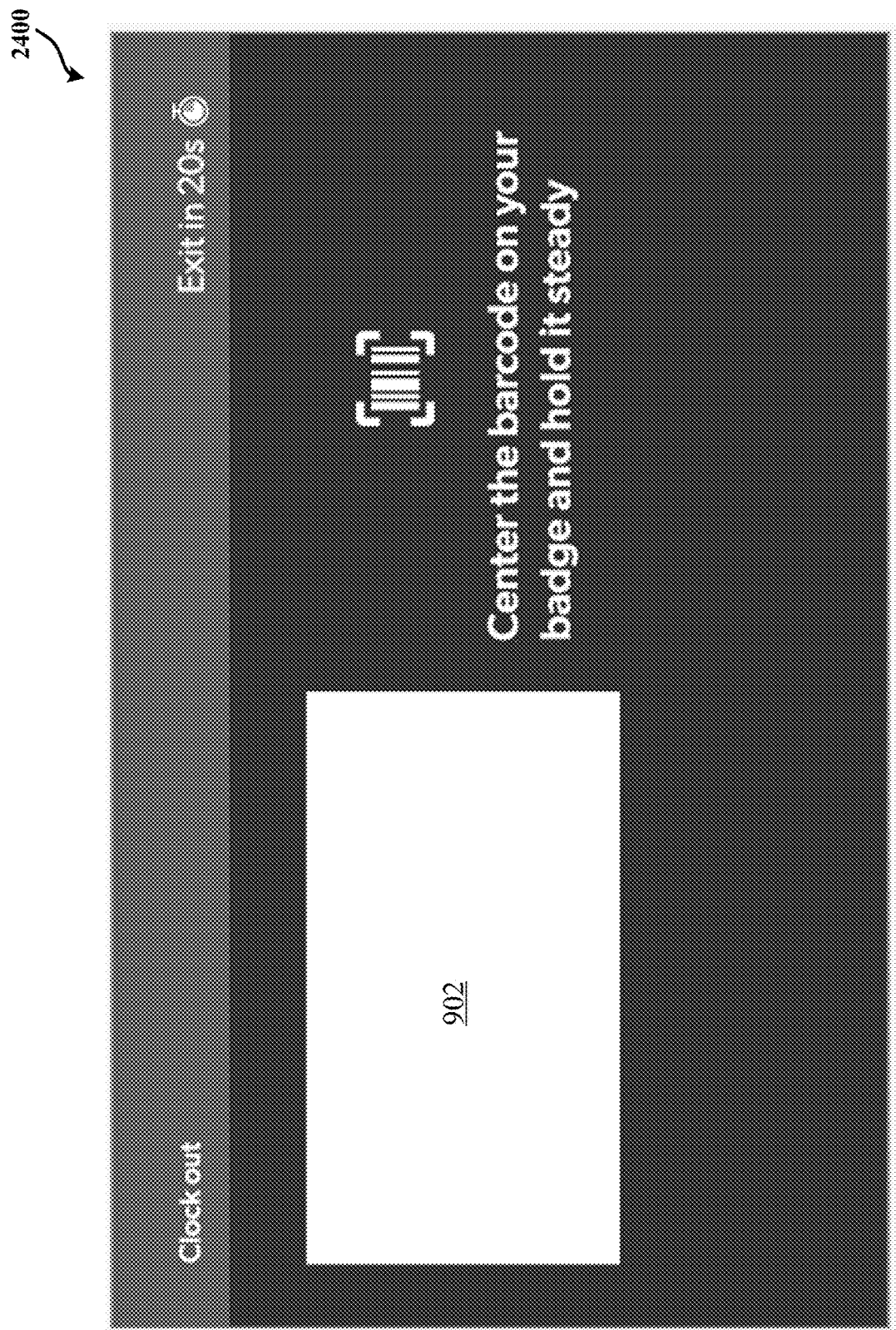
Figure 25:
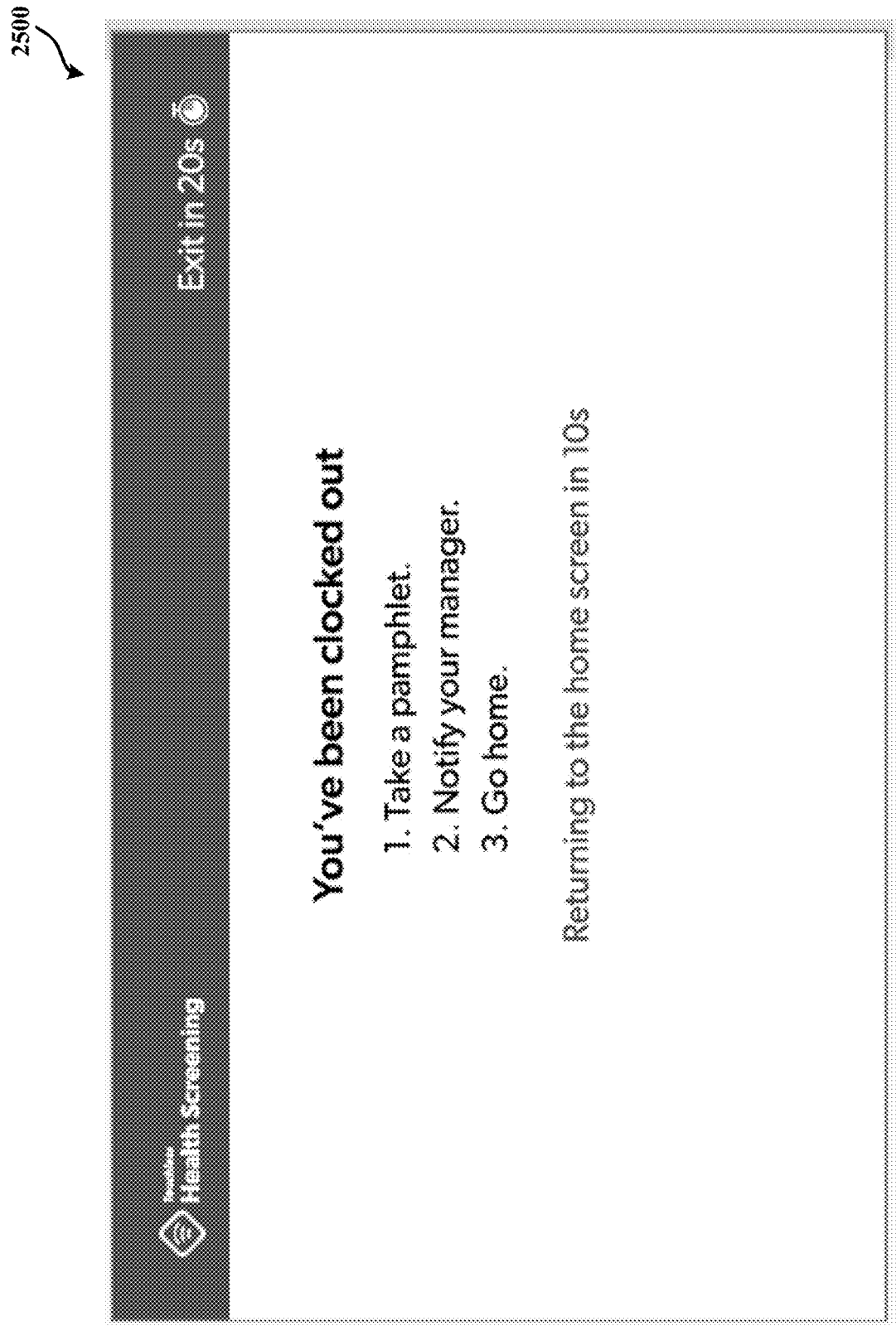
Figure 26:
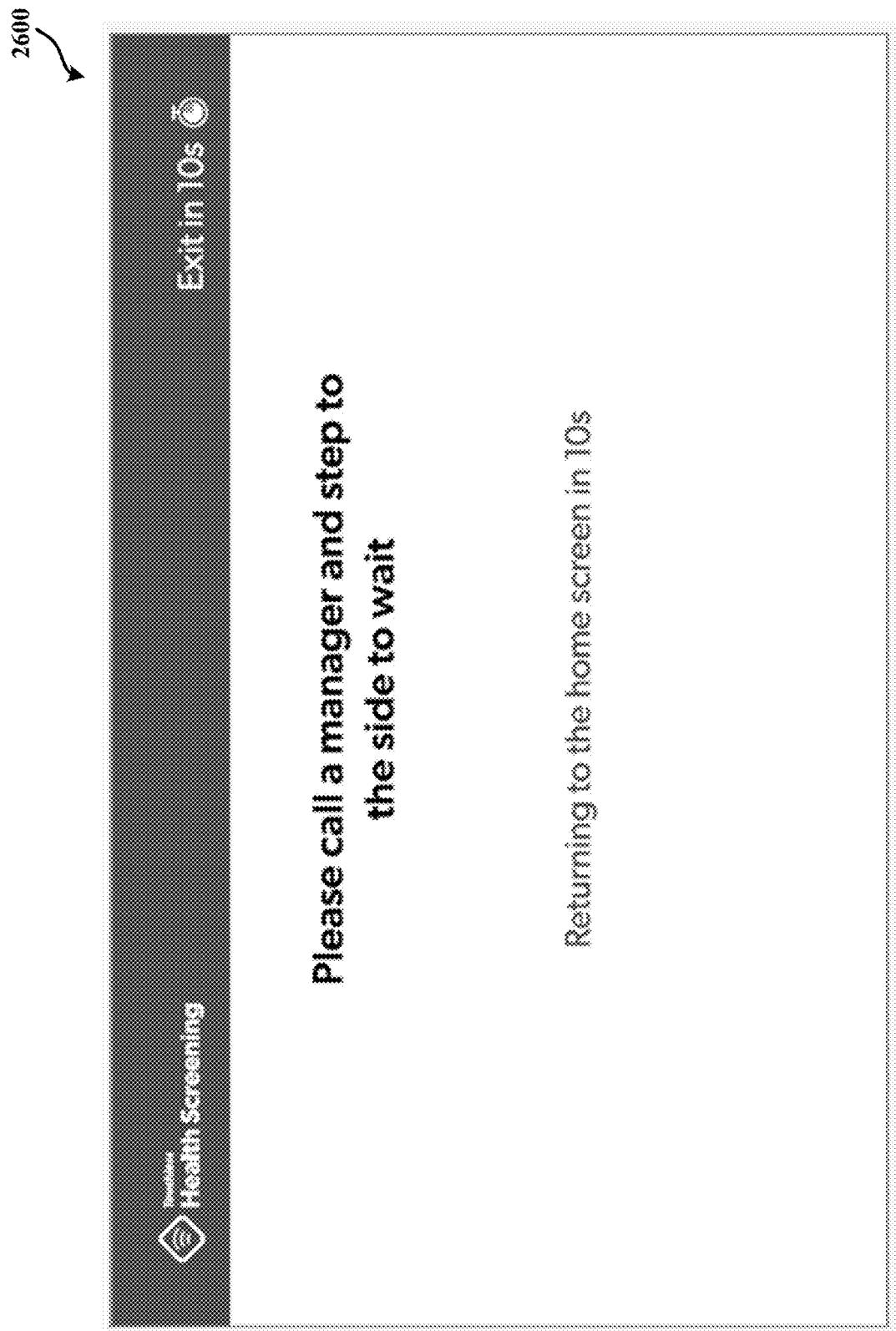

In some embodiments, the human 120 may select an option shown in the graphical user interface 2300 of FIG. 23 to clock out by moving the hand 214 of the human 120 across or in front of the second motion sensor 206. In some embodiments, in response to the selection, the control circuit 102 may cause the graphical user interface of the display 202 to display a graphical user interface 2400 of FIG. 24 instructing the human 120 to scan the barcode of the identification badge. The window portion 902 displays the view as seen by the first image sensor 208 to assist the human in aligning the identification badge. In some embodiments, in response to the selection to clock out, the control circuit 102 may determine a time data corresponding to the time the human 120 scanned the identification badge to clock out indicating the end the work shift. In some embodiments, in response to the selection to clock out, the control circuit 102 may cause the graphical user interface of the display 202 to display a graphical user interface 2500 of FIG. 25 instructing the next action the human 120 is instructed to follow (e.g., take a pamphlet, notify manager, and/or go home). In some embodiments, the control circuit 102 may transmit via the transceiver 114 a time data (e.g., the clock in time and/or the clock out time) to another control circuit (e.g., the server 128) to record in a database 122.

In some embodiments, the human 120 may select an option shown in the graphical user interface 2300 of FIG. 23 to have a second screening by moving the hand 214 of the human 120 across or in front of the first motion sensor 204. In some embodiments, in response to the selection to have the second screening, the control circuit 102 may cause the graphical user interface of the display 202 to display a graphical user interface 2600 of FIG. 26 instructing the human 120 to call a manager and step to the side to wait.

In some embodiments, in the graphical user interface 900 of FIG. 9, the human 120 may select an option for not having a barcode and/or an identification badge by motioning its hand 214 in front of the second motion sensor 206. In some embodiments, in response to the selection of not having the barcode and/or the identification badge, the control circuit 102 causes the graphical user interface of the display 202 to display a graphical user interface 1900 instructing the human 120 to clock in or do a manual time adjustment.

In some embodiments, the human 120 may select an option indicating he/she is already clocked in by moving the hand 214 of the human 120 across or in front of the second motion sensor 206. In some embodiments, in response to a selection, the control circuit 102 causes the graphical user interface of the display 202 to display a graphical user interface 2000 of FIG. instructing the human 120 to trigger the first image sensor 208 to capture an image of the identification badge by moving the hand 214 of the human 120 across or in front of the second motion sensor 206. The window portion 902 displays the view as seen by the first image sensor 208 to assist the human in aligning the identification badge.

In some embodiments, in the graphical user interface 900 of FIG. 9, the human 120 may select an option to clock out by motioning/moving its hand 214 in front of the first motion sensor 204. In some embodiments, in response to the selection, the control circuit 102 causes the graphical user interface of the display 202 to display a graphical user interface 1800 of FIG. 18 instructing the human 120 to scan the identification badge via the first image sensor 208. The window portion 902 displays the view as seen by the first image sensor 208 to assist the human in aligning the identification badge. In some embodiments, the control circuit 102 may determine whether the scanning of the identification badge indicate a clocking in or a clocking out of the human 120 based on at least one of the associated work schedule of the human 120 and the number of times the identification badge has been scanned during a particular period of time.

Figure 8:
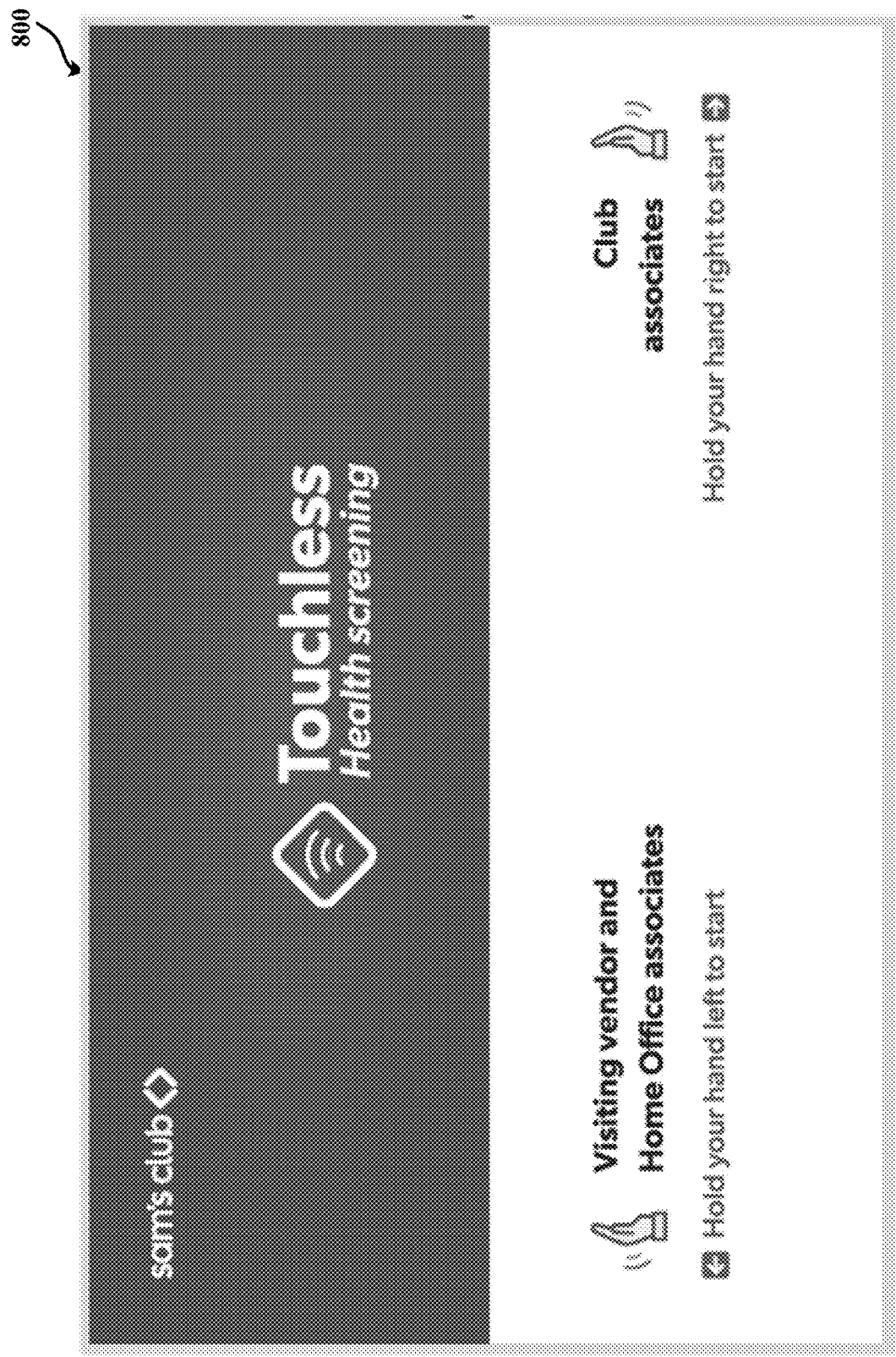

In some embodiments, in the graphical user interface 800 of FIG. 8, the human 120 may select an option for a visiting vendor and home office associates by motioning/moving its hand 214 in front of the first motion sensor 204. In some embodiments, in response to the selection, the control circuit 102 causes the graphical user interface of the display 202 to display a graphical user interface 2000 of FIG. 20 instructing the human 120 to trigger the first image sensor 208 to capture an image of an identification badge by moving the hand 214 of the human 120 across or in front of the second motion sensor 206. The window portion 902 displays the view as seen by the first image sensor 208 to assist the human in aligning the identification badge, card or other information.

Figure 28:
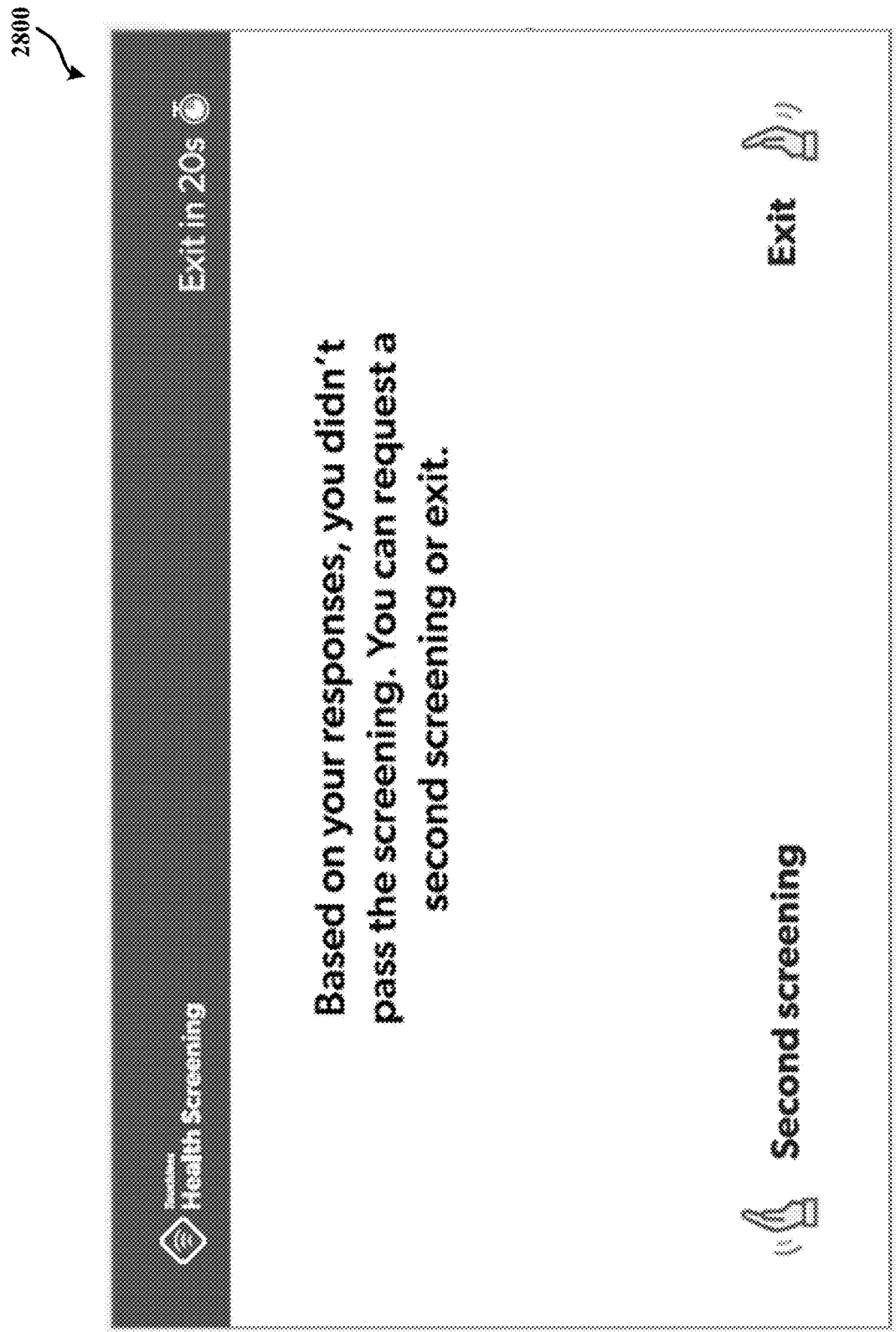
Figure 29:
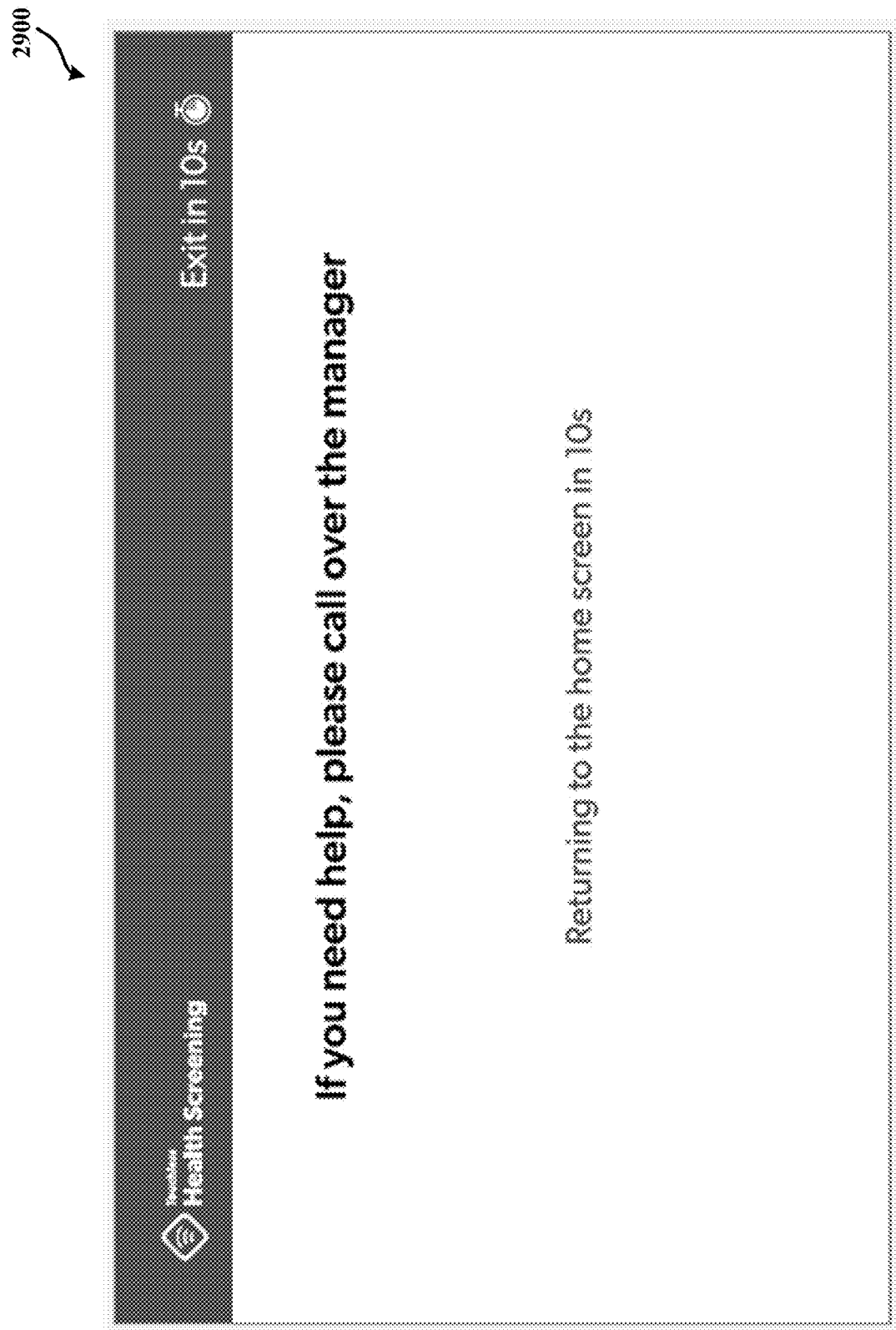
Figure 30:
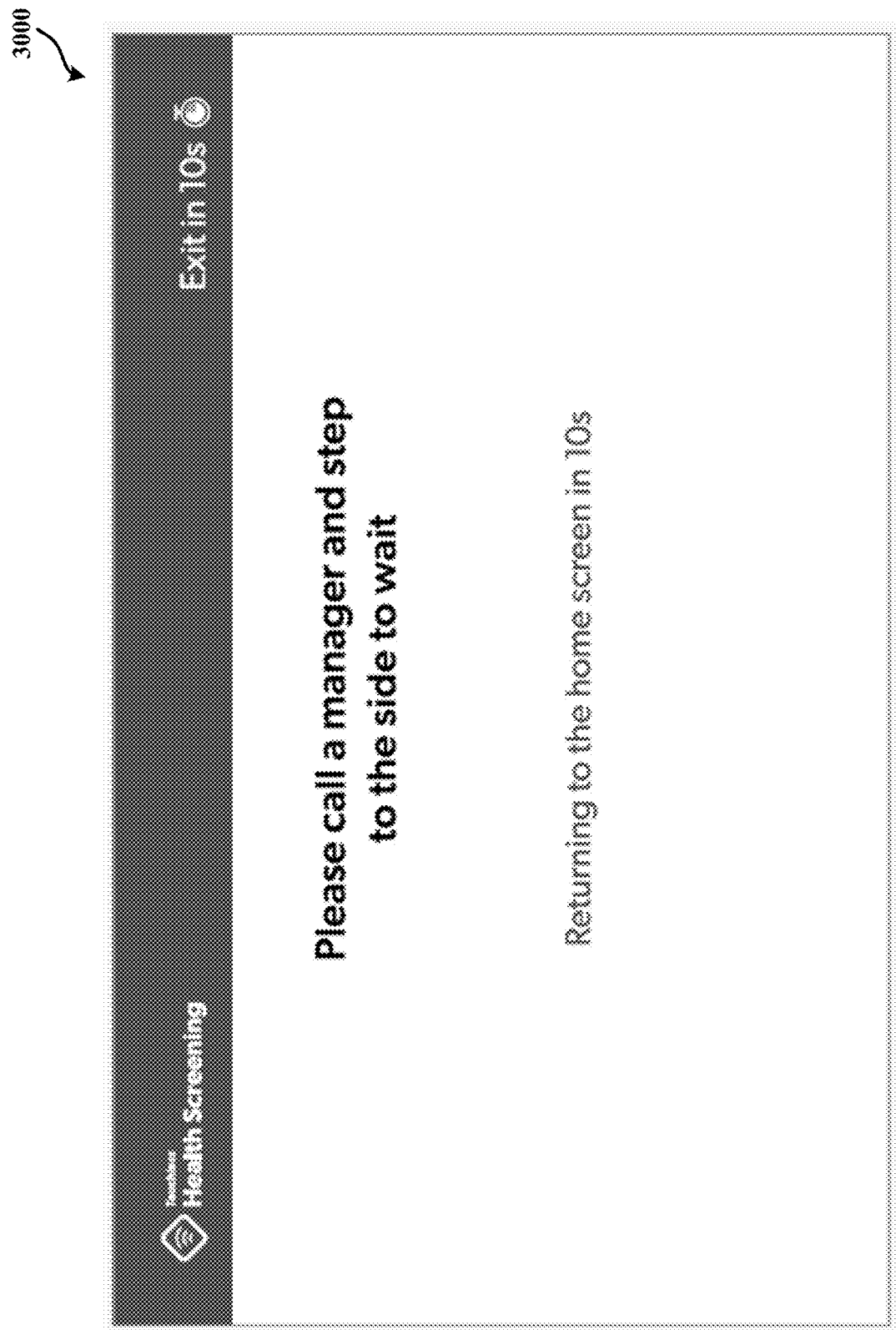

In some embodiments, after affirmatively responding to at least one of the questions shown in FIGS. 12-15 and/or failing to detect and/or read a body temperature that is within the predetermined temperature range, the control circuit 102 causes the graphical user interface of the display 202 to display a graphical user interface 2800 of FIG. 28 instructing the human 120 a couple of options to proceed. In some embodiments, the human 120 may select an option for a second screening by motioning/moving its hand 214 in front of the first motion sensor 204. In some embodiments, in response to the selection, the control circuit 102 causes the graphical user interface of the display 202 to display a graphical user interface 3000 of FIG. 30 instructing the human 120 to call a manager and step aside to wait. Alternatively, the human 120 may select an option to exit in the graphical user interface 2800 of FIG. 28 by motioning/moving its hand 214 in front of the second motion sensor 206. In some embodiments, in response to the selection, the control circuit 102 causes the graphical user interface of the display 202 to display a graphical user interface 2900 of FIG. 29 instructing the human 120 to call a manager if help and/or assistance is needed.

Figure 27:
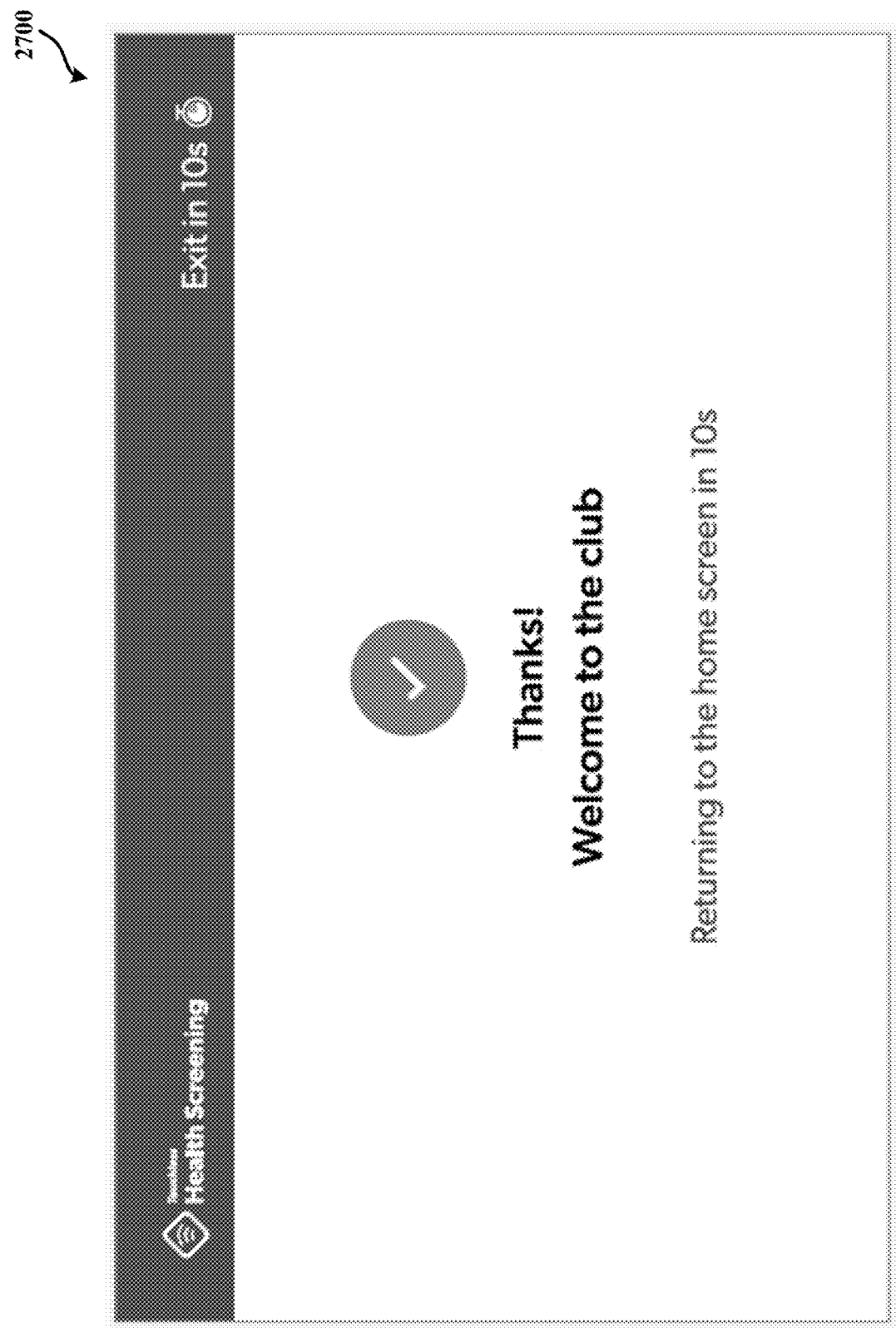

In some embodiments, after negatively responding to all of the questions shown in FIGS. 12-15 and detecting and/or reading a body temperature that is within the predetermined temperature range, the control circuit 102 causes the graphical user interface of the display 202 to display a graphical user interface 2700 of FIG. 27 authorizing the human 120 to enter the facility.

Figure 7:
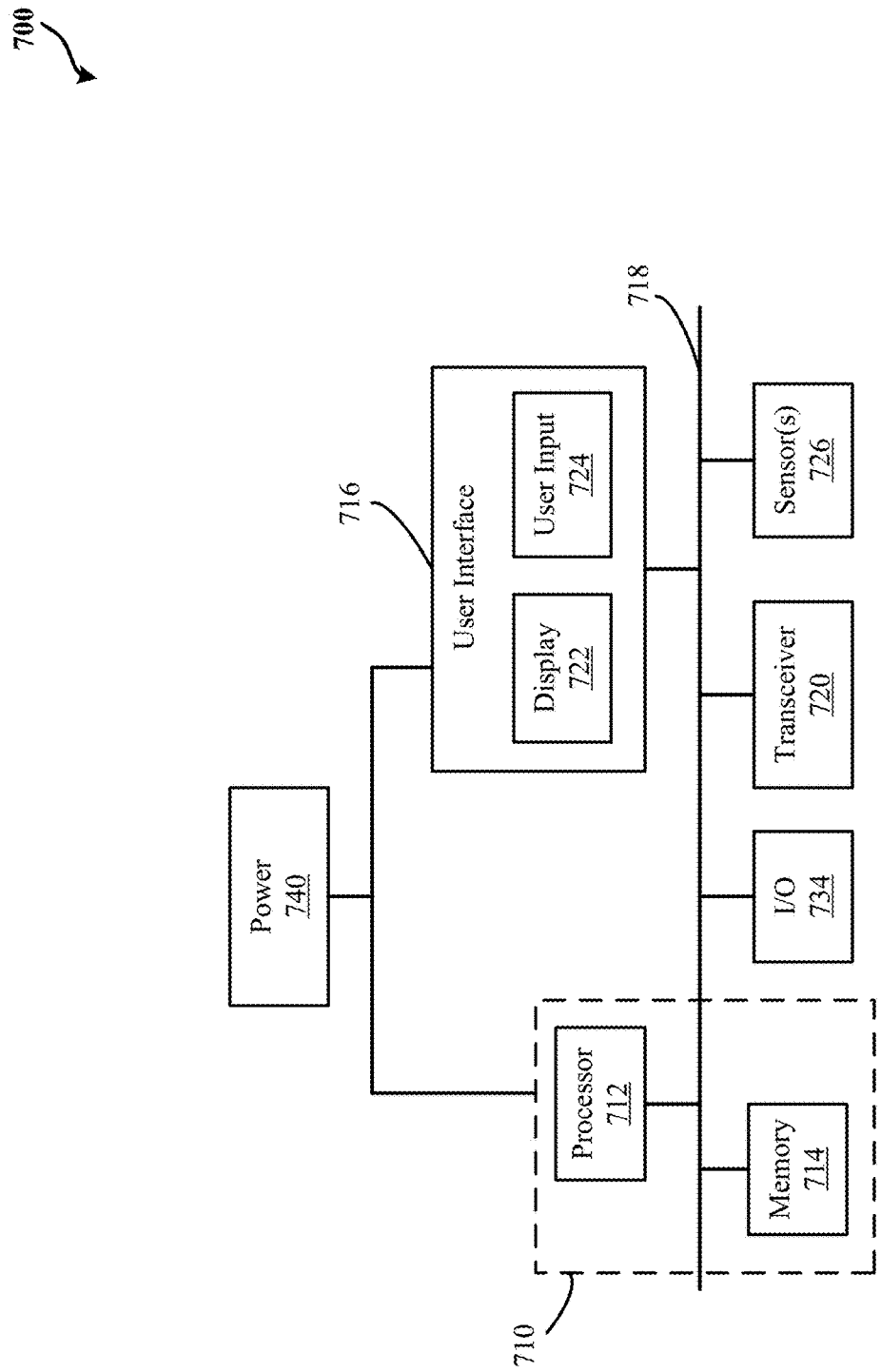
FIG. 7 illustrates an exemplary system for use in implementing methods, techniques, devices, apparatuses, systems, servers, sources and screening of a body temperature of a human, in accordance with some embodiments.

Further, the circuits, circuitry, systems, devices, processes, methods, techniques, functionality, services, servers, sources, and the like described herein may be utilized, implemented and/or run on many different types of devices and/or systems. FIG. 7 illustrates an exemplary system 700 that may be used for implementing any of the components, circuits, circuitry, systems, functionality, apparatuses, processes, or devices of the system 100 of FIG. 1, the system 200 of FIG. 2, the system 300 of FIG. 3, the system 400 of FIG. 4, the system 500 of FIG. 5, the method 600 of FIG. 6, the graphical user interfaces shown in FIGS. 8-30, and/or other above or below mentioned systems or devices, or parts of such circuits, circuitry, functionality, systems, apparatuses, processes, or devices. For example, the system 700 may be used to implement some or all of the systems 100, 200, 300, 400, 500 for a touchless health screening system that screens a body temperature of a human, the output interface 108, the control circuit 102, the transceiver 114, the control I/O device interface 116, the sensors 110, the additional sensors 112, the databases 122, the second communication network 124, the devices 126, the servers 128, the display 202, the first motion sensor 204, the second motion sensor 206, the first image sensor 208, the second image sensor 210, the temperature sensors 212, 402, the communication network 118, and/or other such components, circuitry, functionality and/or devices. However, the use of the system 700 or any portion thereof is certainly not required.

By way of example, the system 700 may comprise a processor module (or a control circuit) 712, memory 714, and one or more communication links, paths, buses or the like 718. Some embodiments may include one or more user interfaces 716, and/or one or more internal and/or external power sources or supplies 740. The control circuit 712 can be implemented through one or more processors, microprocessors, central processing unit, logic, local digital storage, firmware, software, and/or other control hardware and/or software, and may be used to execute or assist in executing the steps of the processes, methods, functionality and techniques described herein, and control various communications, decisions, programs, content, listings, services, interfaces, logging, reporting, etc. Further, in some embodiments, the control circuit 712 can be part of control circuitry and/or a control system 710, which may be implemented through one or more processors with access to one or more memory 714 that can store instructions, code and the like that is implemented by the control circuit and/or processors to implement intended functionality. In some applications, the control circuit and/or memory may be distributed over a communications network (e.g., LAN, WAN, Internet) providing distributed and/or redundant processing and functionality. Again, the system 700 may be used to implement one or more of the above or below, or parts of, components, circuits, systems, processes and the like. For example, the system 700 may implement the system for a touchless temperature screening system that screens a body temperature of a human with the control circuit 102 being the control circuit 712.

The user interface 716 can allow a user to interact with the system 700 and receive information through the system. In some instances, the user interface 716 includes a display 722 and/or one or more user inputs 724, such as buttons, touch screen, track ball, keyboard, mouse, etc., which can be part of or wired or wirelessly coupled with the system 700. Typically, the system 700 further includes one or more communication interfaces, ports, transceivers 720 and the like allowing the system 700 to communicate over a communication bus, a distributed computer and/or communication network (e.g., a local area network (LAN), the Internet, wide area network (WAN), etc.), communication link 718, other networks or communication channels with other devices and/or other such communications or combination of two or more of such communication methods. Further the transceiver 720 can be configured for wired, wireless, optical, fiber optical cable, satellite, or other such communication configurations or combinations of two or more of such communications. Some embodiments include one or more input/output (I/O) interface 734 that allow one or more devices to couple with the system 700. The I/O interface can be substantially any relevant port or combinations of ports, such as but not limited to USB, Ethernet, or other such ports. The I/O interface 734 can be configured to allow wired and/or wireless communication coupling to external components. For example, the I/O interface can provide wired communication and/or wireless communication (e.g., Wi-Fi, Bluetooth, cellular, RF, and/or other such wireless communication), and in some instances may include any known wired and/or wireless interfacing device, circuit and/or connecting device, such as but not limited to one or more transmitters, receivers, transceivers, or combination of two or more of such devices.

In some embodiments, the system may include one or more sensors 726 to provide information to the system and/or sensor information that is communicated to another component, such as the output interface 108, the control circuit 102, the transceiver 114, the control I/O device interface 116, the sensors 110, the additional sensors 112, the databases 122, the second communication network 124, the devices 126, the servers 128, the display 202, the first motion sensor 204, the second motion sensor 206, the first image sensor 208, the second image sensor 210, the temperature sensor 212, 402, the communication network 118, etc. The sensors can include substantially any relevant sensor, such as temperature sensors, distance measurement sensors (e.g., optical units, sound/ultrasound units, etc.), optical based scanning sensors to sense and read optical patterns (e.g., bar codes), radio frequency identification (RFID) tag reader sensors capable of reading RFID tags in proximity to the sensor, and other such sensors. The foregoing examples are intended to be illustrative and are not intended to convey an exhaustive listing of all possible sensors. Instead, it will be understood that these teachings will accommodate sensing any of a wide variety of circumstances in a given application setting.

The system 700 comprises an example of a control and/or processor-based system with the control circuit 712. Again, the control circuit 712 can be implemented through one or more processors, controllers, central processing units, logic, software and the like. Further, in some implementations the control circuit 712 may provide multiprocessor functionality.

The memory 714, which can be accessed by the control circuit 712, typically includes one or more processor readable and/or computer readable media accessed by at least the control circuit 712, and can include volatile and/or nonvolatile media, such as RAM, ROM, EEPROM, flash memory and/or other memory technology. Further, the memory 714 is shown as internal to the control system 710; however, the memory 714 can be internal, external or a combination of internal and external memory. Similarly, some or all of the memory 714 can be internal, external or a combination of internal and external memory of the control circuit 712. The external memory can be substantially any relevant memory such as, but not limited to, solid-state storage devices or drives, hard drive, one or more of universal serial bus (USB) stick or drive, flash memory secure digital (SD) card, other memory cards, and other such memory or combinations of two or more of such memory, and some or all of the memory may be distributed at multiple locations over the computer network. The memory 714 can store code, software, executables, scripts, data, content, lists, programming, programs, log or history data, user information, customer information, product information, and the like. While FIG. 7 illustrates the various components being coupled together via a bus, it is understood that the various components may actually be coupled to the control circuit and/or one or more other components directly.

Various systems, structures, devices and methods are provided herein for assessing a health status of a human. In some embodiments, a touchless temperature screening system that screens a body temperature of a human comprises: a housing comprising an output interface configured to provide one or more messages to a human, wherein the human comprises one of an employee of a retail entity, an employee of a vendor of the retail entity, and a visitor seeking access to a facility of the retail entity; a plurality of sensors coupled to the housing; and a control circuit coupled to the output interface and the plurality of sensors. The at least one of the plurality of sensors is configured to at least one of: capture identification information associated with the human; receive one or more user inputs from the human; and detect a body temperature of the human. And the control circuit is configured to: receive, via at least one of the plurality of sensors, the identification information associated with the human; cause the output interface to provide the one or more messages to the human; receive, via the at least one of the plurality of sensors, the one or more user inputs from the human indicative of responses to at least one of the one or more messages; receive, via the at least one of the plurality of sensors, temperature data corresponding to the body temperature of the human; determine, based on the received one or more user inputs and the received temperature data, whether the human meets a health criteria; and cause the output interface to provide a message of the one or more messages indicating whether the human has met the health criteria.

In some embodiments, a method for touchless temperature screening system that screens a body temperature of a human comprises: receiving, by a control circuit via at least one of a plurality of sensors, an identification information associated with a human, wherein the human comprises one of an employee of a retail entity, an employee of a vendor of the retail entity, and a visitor seeking access to a facility of the retail entity; causing, by the control circuit, an output interface to provide one or more messages to the human; receiving, by the control circuit via at least one of the plurality of sensors, one or more user inputs from the human indicative of responses to at least one of the one or more messages; receiving, by the control circuit via the at least one of the plurality of sensors, temperature data corresponding to a body temperature of the human; determining, by the control circuit based on the received one or more user inputs and the received temperature data, whether the human meets a health criteria; and causing, by the control circuit, the output interface to provide a message of the one or more messages indicating whether the human has met the health criteria.

And in some embodiments, a touchless temperature screening system that screens a body temperature of a human comprises: a housing comprising an output interface configured to provide one or more messages to a human, wherein the human comprises one of an employee of a retail entity, an employee of a vendor of the retail entity, and a visitor seeking access to a facility of the retail entity; a plurality of sensors coupled to the housing; and a control circuit coupled to the output interface and the plurality of sensors. The at least one of the plurality of sensors is configured to at least one of: receive one or more user inputs from the human; and detect a body temperature of the human. And the control circuit is configured to: cause the output interface to provide the one or more messages to the human; receive, via the at least one of the plurality of sensors, the one or more user inputs from the human indicative of responses to at least one of the one or more messages; receive, via the at least one of the plurality of sensors, temperature data corresponding to the body temperature of the human; determine, based on the received one or more user inputs and the received temperature data, whether the human meets a health criteria; and cause the output interface to provide a message of the one or more messages indicating whether the human has met the health criteria.

Figure 31:
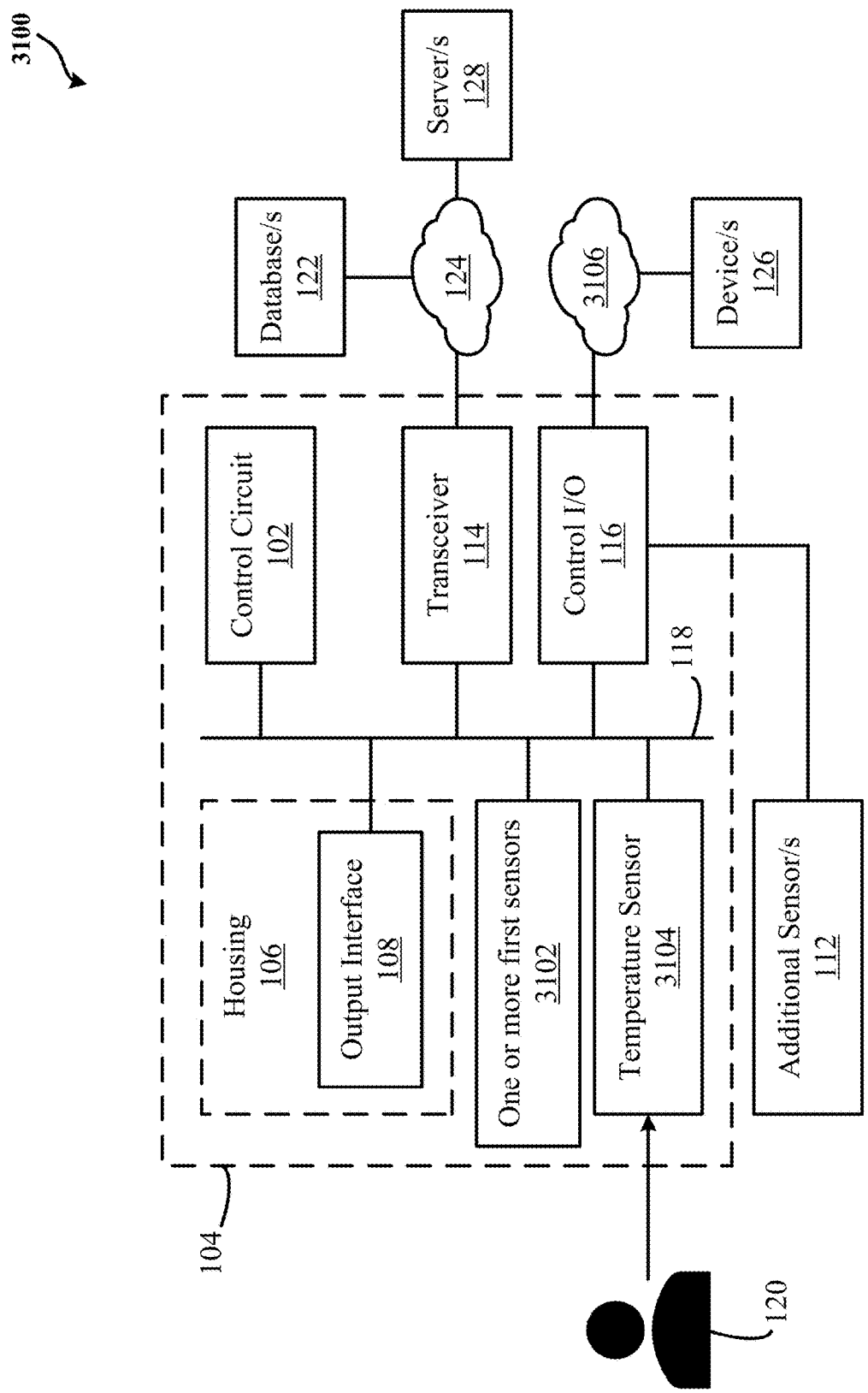
FIG. 31 illustrates a simplified block diagram of an exemplary system for touchless screening of a body temperature of a human in accordance with some embodiments.
Figure 32:
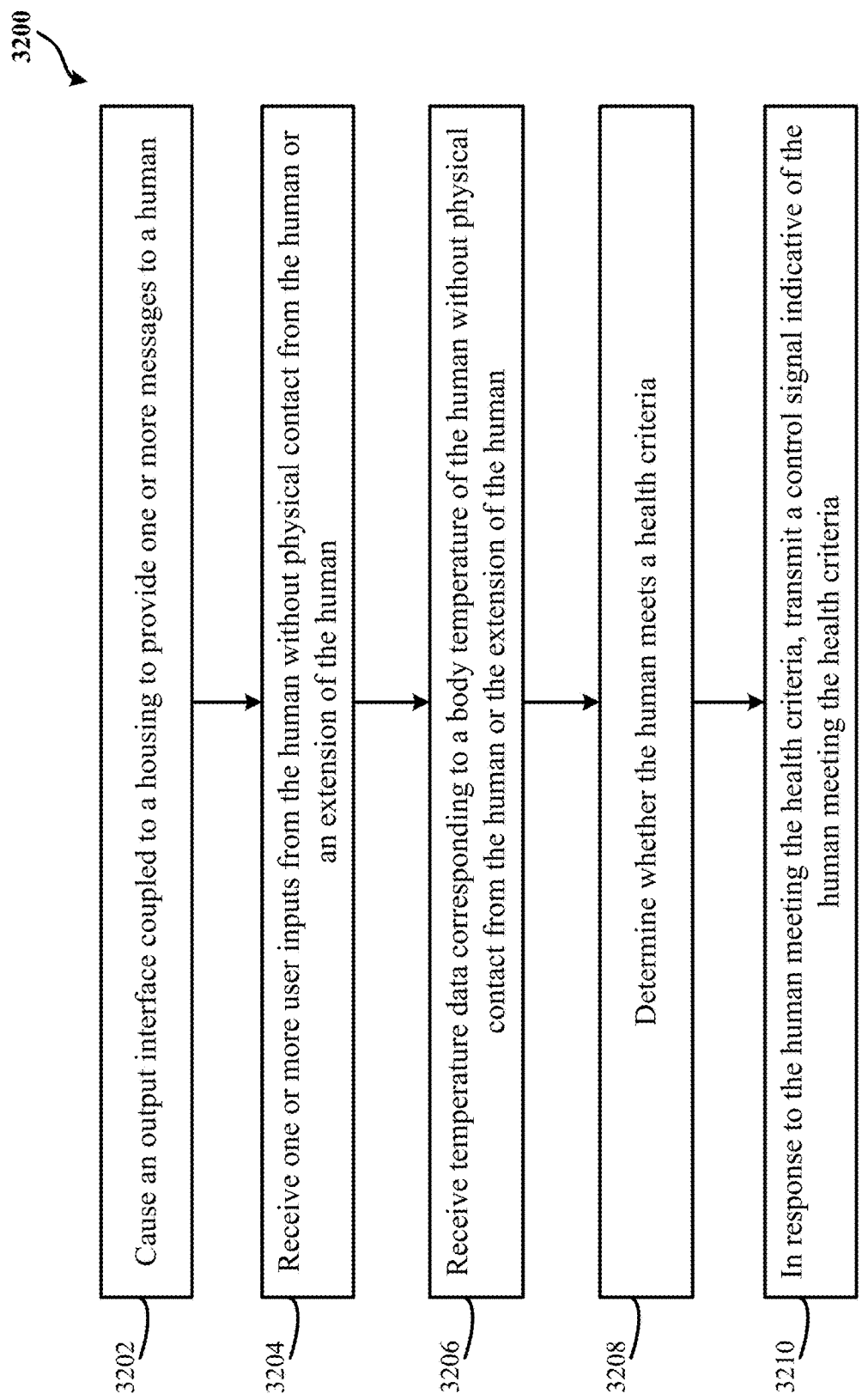
FIG. 32 shows a flow diagram of an exemplary process of touchless screening of a body temperature of a human in accordance with some embodiments.

To further illustrate, FIGS. 31 and 32 are described below. FIG. 31 illustrates a simplified block diagram of an exemplary system 3100 for touchless screening of a body temperature of a human in accordance with some embodiments. FIG. 32 shows a flow diagram of an exemplary process/method 3200 for touchless screening of a body temperature of a human in accordance with some embodiments. In some embodiments, the system 300 of FIG. 3, the system 400 of FIG. 4, and/or the system 500 of FIG. 5 is an illustrative non-limiting exemplary example of the system 3100. In some embodiments, the system 3100 may be an illustrative non-limiting example of the system 100 of FIG. 1 and/or the system 200 of FIG. 2. As such, one or more elements/components/features of other systems described herein, for example, the system 100 of FIG. 1 and the system 200 of FIG. 2, are equally applicable to the system 3100. In some embodiments, the system 3100 includes one or more first sensors 3102 of a plurality of sensors 110 coupled to a housing 106. In some embodiments, the one or more first sensors 3102 includes a gesture sensor, an audio sensor, a distance sensor, an ultrasonic sensor, an electronic sensor, and/or a pedal sensor. In some embodiments, the one or more first sensors 3102 receive one or more user inputs from a human 120 without a direct or indirect physical contact from the human 120 or an extension of the human 120. In some embodiments, the one or more first sensors 3102 receive one or more user inputs from the human 120 without a direct or indirect physical contact from a hand or finger of the human 120 or an extension or covering of the hand or the finger of the human 120. In some embodiments, an extension of the human may correspond to any inanimate object used as an extension of, shield for, or covering of, the human's arm, hand, finger, and/or foot used to indirectly touch and/or physically interact with a device. In some embodiments, the human 120 includes a customer, a passenger, a patient, an employee, a guest, a contractor, a resident, and/or any other humans such those described herein or otherwise depending on the use of the health screening system. In some embodiments, the system 3100 includes a temperature sensor 3104 of the plurality of sensors 110 coupled to the housing 106. In some embodiments, the temperature sensor 3104 include an infrared sensor and/or a thermal camera. In some embodiments, the temperature sensor 3104 detects a body temperature of the human 120 without physical contact from the human 120 or the extension of the human. In some embodiments, the temperature sensor 3104 includes an infrared sensor and/or a thermal camera.

In some embodiments, the system 3100 includes a control circuit 102 coupled to an output interface 108, the one or more first sensors 3102, and/or the temperature sensor 3104. In some embodiments, the control circuit 102 causes, at step 3202, the output interface 108 coupled to the housing 106 to provide one or more messages to the human 120. In some embodiments, the control circuit 102 receives, via the one or more first sensors 3102, the one or more user inputs from the human 120 indicative of responses to at least one of the one or more messages. In some embodiments, the one or more user inputs are received from the human 120 without direct physical contact from a hand or a finger of the human and without indirect physical contact from an extension of, a shield for, or a covering of the hand or the finger of the human, at step 3204. In some embodiments, the one or more user inputs are received from the human 120 without direct physical contact from any portion of the human and without indirect physical contact from an extension of, a shield for, or a covering of the any portion of the human, at step 3206. In some embodiments, the control circuit 102 receives, via the temperature sensor 3104, temperature data corresponding to the body temperature of the human 120, at step 3208.

In some embodiments, the control circuit 102 determines, based on the received one or more user inputs and the received temperature data, whether the human meets a health criteria, at step 3210. In some embodiments, the control circuit 102 transmits, at step 3212, a control signal indicative of the human 120 meeting the health criteria. In some embodiments, the control signal causes the output interface 108 to provide a message of the one or more messages indicating that the human 120 has met the health criteria.

In some embodiments, the system 3100 includes the one or more devices 126. In some embodiments, a device 126 (e.g., a printer) outputs at least one of: a name tag and a ticket indicative of the human 120 meeting the health criteria. In some embodiments, the control signal is received by the printer and causes the printer to output the at least one of: the name tag and the ticket. In some embodiments, a device 126 (e.g., a barrier 126a, a door, a turnstile) enables access to a restricted space by the human 120 in response to receiving the control signal. In some embodiments, the system 3100 includes a device 126 (e.g., a user interface operable on a user device 126b associated with the human 120). In some embodiments, the user device 126b includes a smartphone, a smartwatch, and/or a portable device capable of being easily carried from one place to another. In some embodiments, a user interface may include an executable code stored in a memory storage (e.g., a read only memory, a random access memory, a non-volatile memory, a flash drive, to name a few) of the user device 126b. In some embodiments, the user interface receives the control signal transmitted by the control circuit 102. In some embodiments, in response to receiving the control signal, the user interface causes a display screen of the user device 126b to display a digital code indicative of the human 120 meeting the health criteria. In some embodiments, the digital code includes a QR code, a barcode, and/or the like.

In some embodiments, the system 3100 includes a transceiver 114 coupled to the housing 106 and the user interface. In some embodiments, the user interface communicatively couples with the control circuit 102 via a wireless network 3106 when the user device 126b is in proximity to the control circuit 102. In some embodiments, the wireless network 3106 includes Bluetooth, Wi-Fi, and/or any communication network using publicly available wireless protocol. In some embodiments, the user interface causes a display screen of the user device 126b to display the one or more messages to the human. In some embodiments, the user interface causes the user device 126b to transmit to the transceiver 114 the one or more user inputs via the wireless network 3106. In some embodiments, the system 3100 includes a portable base. In some embodiments, the housing 106 is mounted on the portable base that enables the housing 106 to be movable from one place to another place. In some embodiments, the portable base may include a base that enables the system 3100 to be placed on a counter, at an outside area, and/or be hanged. In some embodiments, the output interface 108, the one or more first sensors 3102, the temperature sensor 3104, and the control circuit 102 is integrated with the housing. In some embodiments, an affirmative or a yes response to any of the one or more messages corresponds to the hand moving across or in front of one of the one or more first sensors 3102. In some embodiments, a negative or a no response to any of the one or more messages corresponds to the hand moving across or in front of another of the one or more first sensors 3102. In some embodiments, the system 3100 includes an additional sensor providing a trigger signal to the temperature sensor

3104 to start detecting the body temperature. In some embodiments, the trigger signal is in response to a receipt of the one or more user inputs prompted by a second message of the one or more messages. In some embodiments, the additional sensor is within a threshold distance to the temperature sensor 3104. In some embodiments, the threshold distance corresponds to about 15 centimeters. In some embodiments, the output interface 108 includes a display screen.

In some embodiments, the system 3100 described above may be used in a cruise ship, a sporting event, a large gathering, a nursing home, a hospital, a clinic, an outpatient medical facility, a distribution center, a small business, at a jobsite, a restaurant, a movie theater, a coffee shop, any place that has some type of restricted access or any place for which access is intended, at an area where there is an automated hand sanitizer, a train, a subway, a ridesharing vehicle (e.g., UBER, Lyft, and/or the like), a taxi, an airport, a school building, a parking lot, and/or an office building, to name a few.

For example, in some embodiments, the system 3100 is used to screen passengers before entering a plane and/or before entering customs and immigration. In some embodiments, the system 3100 can be used to screen and/or count people entering a store, a building, a movie theater, and/or a hospital, for example. In some embodiments, a device 126 (e.g., a printer) can print or make a sticker, a pass, and/or a ticket, for example, to grant entry. In some embodiments, the system 3100 can be coupled to an automatic door locking mechanism, for example, a device 126 (e.g., a barrier 126*a*) to unlock a door for entry or access to a restricted area, such as a parking lot, a train, a subway, an office building, a school building, and/or a jobsite, to name a few. In some embodiments, a power supply of the system 100 of FIG. 1, the system 200 of FIG. 2, the system 300 of FIG. 3, the system 400 of FIG. 4, the system 500 of FIG. 5, and/or the system 3100 of FIG. 31 is provided by a wall plug, a building power, a battery, and/or solar power, for example.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A temperature screening system that screens a body temperature of a human, the temperature screening system comprising:
   a housing comprising a display configured to present one or more messages to the human and disposed in the housing to face a first direction;
   two response sensors configured to receive one or more user inputs from the human responsive to the one or more messages without direct physical contact from a hand or a finger of the human and without indirect physical contact from an extension of, a shield for, or a covering of the hand or the finger of the human, a first of the two response sensors disposed in the housing to face a second direction different than the first direction, and a second of the two response sensors disposed in the housing to face a third direction different than first direction and the second direction;
   a temperature sensor configured to contactlessly detect the body temperature of the human; and
   a control circuit coupled to the display, the two response sensors, and the temperature sensor, the control circuit configured to:
   cause the display to present the one or more messages to the human;
   receive, via the two response sensors, the one or more user inputs from the human indicative of responses to at least one of the one or more messages, wherein each response to the at least one of the one or more messages is based on which one of the two response sensors is activated by the human;
   receive, via the temperature sensor, temperature data corresponding to the body temperature of the human;
   determine, based on the received one or more user inputs and the received temperature data, whether the human meets a health criteria; and
   in response to the human meeting the health criteria, transmit a control signal indicative of the human meeting the health criteria.

2. The temperature screening system of claim 1, wherein the human comprises a customer, a passenger, a patient, an employee, a guest, a contractor, and a resident.

3. The temperature screening system of claim 1, wherein the control signal causes the display to provide a message of the one or more messages indicating the human has met the health criteria.

4. The temperature screening system of claim 1, further comprising a printer configured to output at least one of: a name tag and a ticket indicative of the human meeting the health criteria, wherein the control signal is received by the printer and causes the printer to output at least one of: the name tag and the ticket.

5. The temperature screening system of claim 1, further comprising a barrier configured to enable access to a restricted space by the human in response to receiving the control signal.

6. The temperature screening system of claim 5, wherein the barrier comprises one of a door, a turnstile, a gate, an arm gate, and a revolving door.

7. The temperature screening system of claim 1, further comprising a user interface operable on a user device associated with the human, the user interface configured to:
   receive the control signal; and
   in response to receiving the control signal, cause a display screen of the user device to display a digital code indicative of the human meeting the health criteria.

8. The temperature screening system of claim 7, wherein the digital code comprises a QR code.

9. The temperature screening system of claim 7, wherein the user device comprises a smartphone and a smartwatch.

10. The temperature screening system of claim 1, further comprising a transceiver coupled to the housing and a user interface operable on a user device associated with the human, the user interface configured to:
    communicatively coupling with the control circuit via a wireless network when the user device is in proximity to the control circuit;
    cause a display screen of the user device to display the one or more messages to the human; and
    cause the user device to transmit to the transceiver the one or more user inputs via the wireless network.

11. The temperature screening system of claim 1, wherein each of the two response sensors comprise one of a gesture sensor, an audio sensor, a distance sensor, an ultrasonic sensor, an electronic sensor, and a pedal sensor.

12. The temperature screening system of claim 1, wherein the temperature sensor comprises at least one of an infrared sensor and a thermal camera.

13. The temperature screening system of claim 1, further comprising a portable base, wherein the housing is mounted on the portable base that enables the housing to be movable from one place to another place, wherein the display, the two response sensors, the temperature sensor, and the control circuit is integrated with the housing.

14. The temperature screening system of claim 1, wherein an affirmative or a yes response to any of the one or more messages corresponds to the hand moving across or in front of one of the two response sensors, and wherein a negative or a no response to any of the one or more messages corresponds to the hand moving across or in front of the other one of the two response sensors.

15. The temperature screening system of claim 1, further comprising an additional sensor configured to provide a trigger signal to the temperature sensor to start detecting the body temperature, wherein the trigger signal is in response to a receipt of the one or more user inputs prompted by a second message of the one or more messages, and wherein the additional sensor is within a threshold distance to the temperature sensor.

16. The temperature screening system of claim 15, wherein the threshold distance corresponds to about 15 centimeters.

17. The temperature screening system of claim 1, wherein the one or more user inputs are received from the human without direct physical contact from any portion of the human and without indirect physical contact from an extension of, a shield for, or a covering of any portion of the human.

18. A method for temperature screening system that screens a body temperature of a human, the method comprising:

causing, by a control circuit, a display disposed in a housing of the system to present one or more messages to the human, wherein the display is disposed in the housing to face a first direction;

receiving, by two response sensors, one or more user inputs from the human without direct physical contact from a hand or a finger of the human and without indirect physical contact from an extension of, a shield for, or a covering of the hand or the finger of the human, a first of the two response sensors disposed in the housing to face a second direction different than the first direction, and a second of the two response sensors disposed in the housing to face a third direction different than first direction and the second direction, wherein the one or more user inputs are indicative of responses by the human to at least one of the one or more messages and each response to the at least one of the one or more messages is based on which one of the two response sensors is activated by the human;

receiving, by the control circuit via a temperature sensor, temperature data corresponding to the body temperature of the human;

determining, by the control circuit based on the received one or more user inputs and the received temperature data, whether the human meets a health criteria; and in response to the human meeting the health criteria, transmitting, by the control circuit, a control signal indicative of the human meeting the health criteria.

19. The method of claim 18, wherein each one of the two response sensors comprise one of a gesture sensor, an audio sensor, a distance sensor, an ultrasonic sensor, an electronic sensor, and a pedal sensor.

\* \* \* \* \*